(12) United States Patent
Scarborough et al.

(10) Patent No.: US 6,552,079 B2
(45) Date of Patent: *Apr. 22, 2003

(54) INTEGRIN ANTAGONISTS

(75) Inventors: Robert M. Scarborough, Half Moon Bay, CA (US); Mark Smyth, Foster City, CA (US); Ting Su, Belmont, CA (US); Matthew J. Fisher, Mooresville, IN (US); Joseph A. Jakubowski, Indianapolis, IN (US); John J. Masters, Indianapolis, IN (US); Jeffry Bernard Franciskovich, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 112 days.

This patent is subject to a terminal disclaimer.

(21) Appl. No.: 09/855,448

(22) Filed: May 15, 2001

(65) Prior Publication Data

US 2001/0034369 A1 Oct. 25, 2001

Related U.S. Application Data

(63) Continuation of application No. 09/328,197, filed on Jun. 8, 1999, now Pat. No. 6,245,809, which is a continuation of application No. PCT/US97/22495, filed on Dec. 8, 1997
(60) Provisional application No. 60/040,063, filed on Dec. 9, 1996.

(51) Int. Cl.$^7$ .................... C07C 311/04; A61K 31/18
(52) U.S. Cl. ................ 514/534; 514/538; 514/550; 514/562; 560/13; 560/150; 562/430; 562/439
(58) Field of Search .............. 560/13, 150; 562/430, 562/439; 514/534, 538, 550, 562

(56) References Cited

U.S. PATENT DOCUMENTS

| | | | |
|---|---|---|---|
| 5,519,005 A | 5/1996 | Lider et al. | 514/18 |
| 5,707,994 A | 1/1998 | Ikeda et al. | 544/393 |
| 5,773,646 A | 6/1998 | Chandrakumar et al. | 562/426 |

FOREIGN PATENT DOCUMENTS

| | | |
|---|---|---|
| DE | 195 48 709 A1 | 7/1997 |
| EP | 0 578 083 B1 | 1/1994 |
| WO | WO 94/12181 | 6/1994 |
| WO | WO 97/06791 | 2/1997 |
| WO | WO 97/36859 | 10/1997 |

OTHER PUBLICATIONS

Zablocki, J.A. et al., "Fibrinogen Receptor Antagonists", *Expert Opinion on Investigational Drugs*, 3:437–448 (1994).

Choi, E.T., et al., "Inhibition of Neointimal Hyperplasia by Blocking $\alpha_v\beta_3$ Integrin with a Small Peptide Antagonist GpenGRGDSPCA", *J. Vasc. Surg.* 19:125–134 (1994).

Cook, N.S., et al., "Platelet Glycoprotein IIb/IIIa Antagonists", *Drugs of the Future* 19:135–159 (1994).

T. Weller., et al., "Fibrinogen Receptor Antagonists—A Novel Class of Promising Antithrombotics", *Drugs of the Future* 19:461 (1994).

Hynes, R.O., "Integrins: Versatility, Modulation and Signaling in Cell Adhesion", *Cell* 69:11 (1992).

Yue, T.L., et al., "Osteopontin–Stimulated Vascular Smooth Muscle Cell Migration is Mediated by $\beta_3$ Integrin", *Exp. Cell. Res.* 214:459–464 (1994).

Matsuno, H., "Inhibition of Integrin Function by A Cyclic RGD–Containing Peptide Prvents Neointima Formation", *Circulation* 90:2203–2206 (1994).

Rouslahti, E. and Pierschbacher, M.D., "New Perspectives in Cell Adhesion: RGD and Integrins", *Science* 238:491–497 (1987).

Coller, B.S., "Blockade of Platelet GPIIb/IIIa Receptors as an Antithrombotic Strategy", *Circulation* 92:2373–2380 (1995).

Pfaff, M., et al., "Selective Recognition of Cyclic RGD Peptides of NMR Defined Conformation by $\alpha_{IIb}\beta_3$, $\alpha_v\beta_3$, and $\alpha_5\beta_1$ Integrins", *J. Biol. Chem.* 269:20233–20238 (1994).

*Primary Examiner*—Kathleen K. Fonda
*Assistant Examiner*—Leigh C. Maier
(74) *Attorney, Agent, or Firm*—Knobbe, Martens, Olson & Bear, LLP

(57) ABSTRACT

Novel compounds, their salts and compositions related thereto having activity against mammalian integrins are disclosed. The compounds are useful in vitro or in vivo for preventing or treating thrombotic or restenotic disorders.

23 Claims, No Drawings

INTEGRIN ANTAGONISTS

RELATED APPLICATION DATA

This application is a continuation of U.S. patent application Ser. No. 09/328,197, filed Jun. 8, 1999, now U.S. Pat. No. 6,245,809, which is a continuation of international application number PCT/US97/22495 filed Dec. 8, 1997 under the Patent Cooperation Treaty, which is a continuation-in-part of U.S. patent application Ser. No. 08/762,117 filed Dec. 9, 1996 which was converted to provisional application Ser. No. 60/040,063 on Dec. 9, 1996.

FIELD OF THE INVENTION

This invention relates to novel α-sulfonamido and α-sulfinamido containing carboxylic acid compounds which are potent inhibitors of Arginyl-Glycyl-Aspartyl-(RGD)-dependent integrins. In another aspect, the present invention relates to these α-sulfonamido and α-sulfinamido containing carboxylic acids, their pharmaceutically-acceptable salts, and pharmaceutically-acceptable compositions thereof which are useful as potent inhibitors of integrin adhesive functions in mammals. In yet another aspect, the invention relates to methods for using these inhibitors as therapeutic agents for disease states in mammals characterized by aberrant cellular adhesive disorders that occur during thrombosis and restenosis.

BACKGROUND OF THE INVENTION

Cellular adhesion is believed to play an important role in both thrombus formation and cellular responses to vascular injury, as well as for normal hemostasis. Vascular injury and thrombosis are prevalent during the development and progression of vascular disease states. These include conditions such as atherosclerosis, acute myocardial infarction, chronic stable angina, unstable angina, transient ischemic attacks, stroke, peripheral vascular disease, arterial thrombosis, and conditions induced by interventional procedures such as restenosis following angioplasty.

Cellular adhesions can be characterized as either cell-cell adhesions or cell-matrix adhesions. Cells utilize a variety of cell surface adhesion receptors and adhesive proteins to facilitate these adhesive interactions. For cell-cell type adhesions, platelets play a major role in this type of adhesive interaction that occurs during acute thrombosis. Platelet aggregation, thrombus formation and consolidation of clots mediated by platelets are principally achieved by adhesive protein crosslinking of the platelet glycoprotein (GPIIb-IIIa) also referred to as $\alpha_{IIb}\beta_3$ which is found on the platelet surface. This heterodimeric adhesion receptor is one member of a large family of heterodimeric transmembrane glycoprotein receptors, called integrins (Hynes, R. O., "Integrins: Versatility, Modulation and Signaling in Cell Adhesion", Cell 69:11 (1992)).

Other integrins which may have important cell adhesion functions in thrombosis, hemostasis or in disease states characterized by vascular injury are the vitronectin receptors ($\alpha_v\beta_3$ and $\alpha_v\beta_5$) and the fibronectin receptor ($\alpha_5\beta_1$) In particular, the vitronectin receptor, $\alpha_v\beta_3$, has been postulated to play roles in cellular migration of smooth muscle cells following vascular injury that can ultimately lead to restenosis of the vessel (Yue, T. L., et at., "Osteopontin-Stimulated Vascular Smooth Muscle Cell Migration is Mediated by $\beta_3$ Integrin", Exp. Cell. Res. 214:459–464 (1994); Choi, E. T., et al., "Inhibition of Neointimal Hyperplasia by Blocking $\alpha_v\beta_3$ Integrin with a Small Peptide Antagonist GpenGRGDSPCA", J. Vasc. Surg. 19:125–134 (1994); Matsuno, H., "Inhibition of Integrin Function by A Cyclic RGD-Containing Peptide Prevents Neointima Formation", Circulation 90:2203–2206 (1994)). A number of the natural ligands of these integrins (e.g. $\alpha_{IIb}\beta_3$, $\alpha_v\beta_3$, $\alpha_v\beta_5$, and $\alpha_5\beta_1$) such as fibrinogen, fibronectin, von Willebrand factor, thrombospondin, osteopontin, vitronectin and others, contain and utilize the tripeptide sequence, Arg-Gly-Asp (RGD) to bind to their respective integrins. Small synthetic peptides containing the RGD sequence have been shown to bind to these integrins and to compete for the binding of natural adhesive ligands (Rouslahti, E. and Pierschbacher, M. D.,"New Perspectives in Cell Adhesion: RGD and Integrins", Science 238:491–497 (1987)). Peptides containing the RGD sequence or mimetic compounds have thus been the basis for the discovery of several potent and highly specific inhibitors of platelet $\alpha_{IIb}\beta_3$ which are useful as antithrombotic agents. This literature has been extensively reviewed. See Coller, B. S., "Blockade of Platelet GPIIb/IIIa Receptors as an Antithrombotic Strategy", Circulation 92:2373–2380 (1995); Cook, N. S., et al., "Platelet Glycoprotein IIb/IIIa Antagonists", Drugs of the Future 19:135–159 (1994); T. Weller., et al., "Fibrinogen Receptor Antagonists—A Novel Class of Promising Antithrombotics", Drugs of the Future 19:461 (1994); and Zablocki, J. A., et al., "Fibrinogen Receptor Antagonists", Exp. Opin. Invest. Drugs, 3:437–448 (1994).

Highly specific inhibitors of $\alpha_v\beta_3$ based on the RGD recognition sequence have also been recently described. Specifically, the cyclic peptide, cyclo[Arg-Gly-Asp-D-Phe-Val] is a very potent and specific inhibitor of the vitronectin receptor $\alpha_v\beta_3$ (Pfaff, M., et al., "Selective Recognition of Cyclic RGD Peptides of NMR Defined Conformation by $\alpha_{IIb}\beta_3$, and $\alpha_5\beta_1$ Integrins", J. Biol. Chem. 269:20233–20238 (1994); Jonczyk, A., et al., European Patent Application 578083A2 (1994)).

The present invention describes the preparation of novel compounds which inhibit the adhesive function of various RGD-dependent integrins. More specifically, the novel compounds are non-specific inhibitors of the platelet integrin $\alpha_{IIb}\beta_3$ and the vitronectin receptor $\alpha_v\beta_3$.

SUMMARY OF THE INVENTION

The present invention relates to novel α-sulfonamido and α-sulfinamido containing carboxylic acids or carboxylic esters, their pharmaceutically-acceptable .stereoisomers, salts, hydrates, solvates and prodrug derivatives, and pharmaceutically-acceptable compositions thereof which have particular biological properties and are useful as potent antithrombotics and/or antirestenotic agents in mammals.

The present invention provides a compound of the formula:

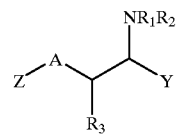

wherein:
Y is selected from the group consisting of —COOH, —PO$_3$H$_2$, —SO$_3$H and —COOR$^4$; where R$^4$ is selected from the group consisting of C$_{1-10}$alkyl, C$_{1-8}$alkylaryl, aryl-C$_{1-8}$alkyl, C$_{1-8}$alkyloxycarbonyloxy-C$_{1-8}$alkyl, aryloxycarbonyloxy-C$_{1-8}$alkyl, $C_{1-8}$alkyloxycarbonyloxyaryl, $C_{1-8}$alkylcarbonyloxy-$C_{1-8}$alkyl, arylcarbonyloxy-$C_{1-8}$alkyl and $C_{1-8}$alkylcarbonyloxyaryl;

A is selected from the group consisting of $C_{6-12}$alkyl, $C_{0-8}$alkyl-$NR^5$—CO—$C_{0-8}$alkyl, $C_{0-8}$-alkyl-CO—$NR^5$—$CO_{0-8}$alkyl, $C_{0-8}$alkyl-O—$C_{0-8}$-alkyl, $C_{0-8}$alkyl-$NR^5$—CO—$C_{0-8}$alkyl-$NR^5$-CO—$C_{0-8}$alkyl, $C_{0-8}$alkyl-$NR^5$—CO—$C_{1-8}$alkyl-CO—$NR^5$—$C_{0-8}$alkyl, $C_{0-8}$alkyl-CO—$NR^5$-$C_{1-8}$alkyl-$NR^5$—CO—$C_{0-8}$alkyl, $C_{0-8}$alkyl-CO—$NR^5$—$C_{0-8}$alkyl-CO—$NR^5$—CO-alkyl, $Cll_8$alkyl-CO—$C_{1-8}$alkyl-CO—$NR^5$—$C_{0-8}$alkyl, $C_{0-8}$alkyl-CO—$C_{0-8}$alkyl-$NR^5$—CO—$C_{0-8}$alkyl, $C_{0-8}$alkyl-O—$C_{2-8}$alkyl-$NR^5$—CO—$C_{0-8}$alkyl, $C_{0-8}$alkyl-O—$C_{0-8}$alkyl-CO—$NR^5$-$C_{0-8}$alkyl, $C_{0-8}$alkyl-O—$C_{2-8}$alkyl-O—$C_{0-8}$alkyl-CO—$NR^5$-CO-alkyl, $C_{0-8}$alkyl-S—$C_{0-8}$alkyl, $C_{0-8}$alkyl-S($O_n$)-$C_{0-8}$alkyl, $C_{0-8}$alkyl-S—$C_{2-8}$alkyl-$NR^5$—CO—$C_{0-8}$alkyl, $C_{0-8}$alkyl-S($O_n$)-$C_{2-8}$alkyl-$NR^5$—CO—$C_{0-8}$alkyl, $C_{0-8}$alkyl-S—$C_{0-8}$alkyl-CO—$NR^5$—$C_{0-8}$alkyl, $C_{0-8}$alkyl-S($O_n$)-$C_{1-8}$-alkyl-CO—$NR^5$—$C_{0-8}$alkyl, $C_{0-8}$alkyl-$NR^5$—CO—$C_{0-8}$alkyl-S—$C_{0-8}$alkyl, $C_{0-8}$alkyl-$NR^5$—CO—$C_{0-8}$alkyl-S($O_n$)-$C_{1-8}$alkyl, $C_{0-8}$alkyl-CO—$NR^5$-$C_{2-8}$alkyl-S—$C_{0-8}$-alkyl, $C_{0-8}$alkyl-CO—$NR^5$-$C_{2-8}$alkyl-S($O_n$)-$C_{0-8}$alkyl, $C_{0-8}$alkyl-$NR^5$-$C_{0-8}$alkyl-$CO_2$—$C_{0-8}$alkyl, $C_{0-8}$alkyl-$NR^5$-$C_{0-8}$alkyl-CS-O—$C_{0-8}$alkyl, $C_{0-8}$alkyl-$NR^5$-$C_{0-8}$alkyl-CO—$NR^5$-$C_{0-8}$alkyl, $C_{0-8}$alkyl-$NR^5$-$C_{0-8}$alkyl-CS-$NR^5$—$C_{0-8}$alkyl, $C_{0-8}$alkyl-O—$C_{0-8}$alkyl-$CO_2$—$C_{0-8}$alkyl, $C_{0-8}$alkyl-O—$C_{0-8}$alkyl-CS-O—$C_{0-8}$alkyl; $C_{0-8}$alkyl-$SiR^7R^8$-alkyl, $C_{0-8}$alkyl-$SiR^7R^8$—$C_{0-8}$alkyl-$NR^6$—CO—$C_{0-8}$alkyl, and $C_{0-8}$alkyl-$SiR^7R^8$-$C_{0-8}$alkyl-CO—NR—CO-alkyl; where $R^5$, $R^6$, $R^7$ and $R^8$ are independently selected from the group consisting of H and $C_{1-6}$alkyl; and where n=1 or 2;

Z is selected from the group consisting of —NH—C($NR^9R^{10}$)=$NR^{11}$, —NH—C($R^9$)=$NR^{11}$, —C($NR^9R^{10}$)=$NR^{11}$ and piperidinyl; where $R^9$, $R^{10}$ and $R^{11}$ are independently selected from the group consisting of H, $C_{1-6}$alkyl, aryl-$C_{1-3}$alkyl and aryl; or where two of the $R^9$, $R^{10}$ or $R^{11}$ substituents form a cyclic ring containing $(CH_2)_p$, where p=2–5;

$R^1$ is H;

$R^2$ is selected from the group consisting of —$SO_m$-aryl, —$SO_m$—$C_{1-10}$alkyl and —$SO_m$-heteroaryl, where m=1–2;

$R^3$ is selected from the group consisting of H, $C_{1-8}$alkyl, aryl, $C_{1-8}$alkylaryl and heteroaryl;

and all pharmaceutically-acceptable stereoisomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically-effective amount of the compounds of this invention and a pharmaceutically-acceptable carrier. In yet another aspect, the present invention includes methods which comprise administering the compounds of the present invention and pharmaceutical compositions thereof for preventing or treating disease states characterized by thrombosis or vascular injury in mammals. Optionally, the methods of this invention comprise administering such pharmaceutical compositions in combination with an additional therapeutic agent such as an antithrombotic, a thrombolytic agent or an anticoagulant, or any combination thereof.

The preferred compounds also include their pharmaceutically-acceptable stereoisomers, hydrates, solvates, salts and prodrug derivatives.

DETAILED DE4SCRIPTION OF THE INVENTION

Definitions

In accordance with the present invention and as used herein, the following terms are defined with the following meanings, unless explicitly stated otherwise.

The term "alkyl" refers to saturated and unsaturated aliphatic groups including straight-chain and branched-chain and cyclic groups, or any combination thereof, having the number of carbon atoms specified, or if no number is specified, having up to 12 carbon atoms. Cyclic alkyls typically comprise a monocyclic aliphatic ring having 3 to 12 carbon atoms and preferably 3 to 7 carbon atoms. The cyclic alkyls of this invention may include one or more nitrogen atoms. Preferably, "alkyl" refers to straight-chain and branched-chain groups; more preferably straight-chain groups.

The term "aryl" refers to an unsubstituted or substituted aromatic ring, substituted with one, two or three substituents selected from $C_{1-6}$alkoxy, $C_{1-6}$alkyl, $C_{1-6}$alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, $C_{1-6}$alkylphenyl, naphthyl, biphenyl, phenanthrenyl, naphthacenyl, and aromatic heterocyclics. The term "heteroaryl" as used herein refers to any aryl group, containing from one to four heteroatoms, selected from the group consisting of nitrogen, oxygen and sulfur.

The term "arylalkyl" refers to one, two, or three aryl groups appended to an alkyl group having the number of carbon atoms designated. Suitable arylalkyl groups include, but are not limited to, benzyl, picolyl, naphthylmethyl, phenethyl, benzhydryl, trityl, and the like, all of which may be optionally substituted. Similarly, the term "alkylaryl" refers to an alkyl group, having the number of carbon atoms designated, appended to one, two, or three aryl groups.

The terms "halo" or "halogen" as used herein refer to Cl, Br, F or I substituents.

The term "oxy" refers to an oxygen (O) atom. The terms "alkyloxy" and "aryloxy" thus refer to the respective groups positioned adjacent to an oxygen atom. The term carbonyloxy refers to —C(O)—O—.

The term "pharmaceutically-acceptable salts" includes salts of compounds derived from the combination of a compound of the present invention and an organic or inorganic acid. These compounds are useful in both free base and salt form. In practice, the use of the salt form amounts to use of the base form; both acid and base addition salts are within the scope of the present invention.

"Pharmaceutically-acceptable acid addition salt" refers to those salts which retain the biological effectiveness and properties of the free bases and which are not biologically or otherwise undesirable, formed with inorganic acids such as hydrochloric acid, hydrobromic acid, hyroiodic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically-acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically-acceptable organic nontoxic bases include salts of primary, secondary, and tertiary amines, substituted amines including naturally occurring substituted amines, cyclic amines and basic ion-exchange resins, such as isopropylamine, trimethylamine, diethylamine, triethylamine, tripropylamine, ethano,amine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

The term "prodrug derivatives" refers to compounds of the invention which have metabolically cleavable groups and become, by sovolysis or under physiological conditions, compounds of the invention which are pharmaceutically-active in vivo. Fro example, ester derivatives of compounds of this invention are often active in vivo, but may have only weak or no activity in vitro. Other derivatives of the compounds of this invention have activity in both their acid and acid derivative forms, but the acid derivative form often offers advantages of solubility, tissue compatibility, or delayed release in the mammalian organism. See Bundgard, H., "Design of Prodrugs", pp. 7–9, 21–24, Elsevier, Amsterdam, 1985. Prodrugs include acid derivatives well known to practitioners of the art, such as esters prepared by the reaction of the parent acid with a suitable alcohol, or amides prepared by reaction of the parent acid with an amine. Simple aliphatic or aromatic esters derived from acidic groups pendant on the compounds of this invention are preferred prodrug derivatives. In some cases, it is desirable to prepare double ester-type prodrugs such as (aclyoxy) alkyl esters or [(alkoxycarbonyl)oxy]alkyl esters.

"Biological property" for the purposes herein means an in vivo effector or antigenic function or activity that is directly or indirectly performed by a compound of this invention. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In addition, the following are used in this application:

"Boc" t-butoxycarbonyl

"BOP" benzotriazol-1-yloxy-tris-(dimethylamino) phosphonium hexafluorophosphate

"Cbz" benzyloxycarbonyl

"DCC" N,N'-dicyclohexylcarbodiimide

"DIEA" diisopropylethylamine

"DMAP" 4-dimethylaminopyridine

"DMF" N,N-dimethylformamide

"HBTU" 2-(1-H-benzotriazol-1-yl)-1,1,3,3,-tetramethyluronium hexafluorophosphate "HF" hydrogen fluoride "HOBt" N-hydroxybenzotriazole "MeOH" methanol "Ph" phenyl "PhSO$_2$NH—" phenylsulfonamido "TFA" trifluoroacetic acid In the compounds of this invention, carbon atoms bonded to four non-identical substituents are asymmetric. Accordingly, the compounds may exist as stereoisomers, including enantiomers and diastereomers. The compounds of this invention having one or more centers of asymmetry may exist as enantiomers or mixtures thereof (e.g. racemates). In addition, compounds that have two or more asymmetric centers can exist as diastereomers. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using methods known in the art. See for example, Jacqes, Collet and Wilen "Enantiomers, Racemates and Resolutions" (Krieger Publishing Co., Malabar, Fla. 1991). Each of the asymmetric centers, when present in the compounds of this invention, may be in one of two configurations (R or S), and both are within the scope of the present invention. Some of the compounds may be designated either D or L, which is a less preferred indicator of the configuration of the compound, based on the compound of this invention having a configuration that is similar to known amino acids. In the processes described above, the final products may, in some cases, contain a small amount of the products having D or L-form residues; however, these products do not affect their therapeutic or diagnostic application.

In all of the compounds of the invention having one or more amide linkages (—CO—NH—), such amide linkages may optionally be replaced with another linkage which is an isostere such as —CH$_2$NH—, —CH$_2$S—, CH$_2$—O, CH$_2$CH$_2$, —CH=CH— (cis and trans), —COCH$_2$—, —CH (OH)CH$_2$—, —CH$_2$SO—, and CH$_2$SO$_2$. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids, Peptides and Proteins," B. Weinstein, eds., Marcel Dekker, New York, p. 267 (1983) (general review); Morley, J. S., *Trends Pharm Sci* pp. 463–468 (1980) (general review); Hudson, D., et al., *Int J Pept Prot Res* 14:177–185 (1979) (—CH$_2$NH—, —CH$_2$CH$_2$—); Spatola, A. F., et al., *Life Sci* 38:1243–1249 (1986) (—CH$_2$—S); Hann, M. M., *J Chem Soc Perkin Trans I* pp. 307–314 (1982) (—CH=CH—, cis and trans); Almquist, R. G., et al., *J Med Chem* 23:1392–1398 (1980) (—COCH$_2$—); Jennings-White, C., et al., *Tetrahedron Lett* 23:2533(1982) (—COCH$_2$—); Szelke, M., et al., European Application EP 45665; CA 97:39405 (1982) (—CH(OH) CH$_2$—); Holladay, M. W., et al., *Tetrahedron Lett* 24:4401–4404 (1983) (—C(OH)CH$_2$—); and Hruby, V. J., *Life Sci* 31:189–199 (1982) (—CH$_2$—S—).

Preferred Embodiments

In preferred embodiments, the present invention provides compounds of the formula:

$$Z-A-\underset{R_3}{\underset{|}{CH}}-\underset{}{\overset{NR_1R_2}{\overset{|}{CH}}}-Y$$

wherein:
- Y is selected from the group consisting of —COOH, —PO$_3$H$_2$, —SO$_3$H and —COOR$^4$; where R$^4$ is selected from the group consisting of C$_{1-10}$alkyl, C$_{1-8}$alkylaryl, aryl-C$_{1-8}$alkyl, C$_{1-8}$alkyloxycarbonyloxy-C$_{1-8}$alkyl, aryloxycarbonyloxy-C$_{1-8}$alkyl, C$_{1-8}$alkyloxycarbonyloxyaryl, C$_{1-8}$alkylcarbonyloxy-C$_{1-8}$alkyl, arylcarbonyloxy-C$_{1-8}$alkyl and C$_{1-8}$alkylcarbonyloxyaryl;
- A is selected from the group consisting of C$_{6-12}$alkyl, C$_{0-8}$alkyl-NR$^5$—CO—C$_{0-8}$alkyl, C$_{0-8}$alkyl-CO—NR$^5$-C$_{0-8}$alkyl, C$_{0-8}$alkyl-O—C$_{0-8}$alkyl, C$_{0-8}$alkyl-NR$^5$—CO—C$_{1-8}$alkyl-NR$^5$—CO—C$_{0-8}$alkyl, C$_{0-8}$alkyl-NR$^5$—CO—C$_{1-8}$alkyl-CO—NR$^5$—C$_{0-8}$-alkyl, C$_{0-8}$alkyl-CO—NR$^5$-C$_{1-8}$alkyl-NR$^5$—CO—C$_{0-8}$alkyl, C$_{0-8}$alkyl-CO—NR$^5$—C$_{0-8}$alkyl-CO—NR$^5$—C$_{0-8}$alkyl, C$_{0-8}$alkyl-CO—C$_{1-8}$alkyl-CO—NR$^5$—C$_{0-8}$alkyl, C$_{0-8}$alkyl-CO—C$_{0-8}$alkyl-NR$^5$—CO—C$_{0-8}$-alkyl, C$_{0-8}$alkyl-O—C$_{2-8}$alkyl-NR$^5$—CO—C$_{0-8}$alkyl, C$_{0-8}$alkyl-O—C$_{0-8}$alkyl-CO—NR$^5$-C$_{0-8}$alkyl, C$_{0-8}$alkyl-O—C$_{2-8}$alkyl-O—C$_{0-8}$alkyl-CO—NR$^5$—C$_{0-8}$alkyl, C$_{0-8}$alkyl-S—C$_{0-8}$alkyl, C$_{0-8}$alkyl-S(O$_n$)—C$_{0-8}$alkyl, C$_{0-8}$alkyl-S—C$_{2-8}$alkyl-NR$^5$—CO—C$_{0-8}$alkyl, C$_{0-8}$alkyl-S(O$_n$)—C$_{2-8}$alkyl-NR$^5$—CO—C$_{0-8}$alkyl, C$_{0-8}$alkyl-S—C$_{0-8}$alkyl-CO—NR$^5$—C$_{0-8}$alkyl, C$_{0-8}$alkyl-S(O$_n$)—C$_{1-8}$alkyl-CO—NR$^5$—C$_{0-8}$alkyl, C$_{0-8}$alkyl-NR$^5$—CO—C$_{0-8}$alkyl-S—C$_{0-8}$alkyl, C$_{0-8}$alkyl-NR$^5$—CO—C$_{1-8}$alkyl-S(O$_n$)—C$_{0-8}$alkyl, C$_{0-8}$alkyl-CO—NR$^5$-C$_{2-8}$alkyl-S—C$_{0-8}$alkyl, C$_{0-8}$alkyl-CO—NR-C$_{2-8}$alkyl-S(O$_n$)-C$_{0-8}$alkyl, C$_{0-8}$alkyl-NR$^5$—C$_{0-8}$alkyl-CO$_2$-C$_{0-8}$alkyl, C$_{0-8}$alkyl-NR$^5$-C$_{0-8}$alkyl-CS—O—C$_{0-8}$alkyl, C$_{0-8}$alkyl-NR$^5$-C$_{0-8}$alkyl-CO—NR$^5$-C$_{0-8}$alkyl, C$_{0-8}$alkyl-NR$^5$-C$_{0-8}$alkyl-CS—NR$^5$-C$_{0-8}$alkyl, C$_{0-8}$alkyl-O—C$_{0-8}$alkyl-CO$_2$-C$_{0-8}$alkyl, C$_{0-8}$alkyl-O—C$_{0-8}$-alkyl-CS—O—C$_{0-8}$-alkyl; C$_{0-8}$alkyl-SiR$^7$R$^8$-C$_{0-8}$alkyl, C$_{0-8}$alkyl-SiR$^7$R$^8$-C$_{0-8}$alkyl-NR$^6$—CO—C$_{0-8}$alkyl, and C$_{0-8}$alkyl-SiR$^7$R$^8$-C$_{0-8}$alkyl-CO—NR$^6$-C$_{0-8}$alkyl; where R$^5$, R$^6$, R$^7$ and R$^8$ are independently selected from the group consisting of H and C$_{1-6}$alkyl; and where n=1 or 2;
- Z is selected from the group consisting of —NH—C(NR$^9$R$^0$)=NR$^{11}$, —NH—C(R$^9$)=NR, —C(NR$^9$R$^{10}$)=NR$^{11}$ and piperidinyl; where R$^9$, R$^{10}$ and R$^{11}$ are independently selected from the group consisting of H, C$_{1-6}$alkyl, aryl-C$_{1-3}$alkyl and aryl; or where two of the R$^9$, R$^{10}$ or R$^{11}$ substituents form a cyclic ring containing (CH$_2$)$_p$, where p=2–5;
- R$^1$ is H;
- R$^2$ is selected from the group consisting of —SO$_m$-aryl, —SO$_m$—C$_{1-10}$alkyl and —SO$_m$-heteroaryl, where m=1–2;
- R$^3$ is selected from the group consisting of H, C$_{1-8}$alkyl, aryl, C$_{1-8}$alkylaryl and heteroaryl;
- and all pharmaceutically-acceptable stereoisomers, salts, hydrates, solvates and prodrug derivatives thereof.

It is understood that the "A" substituents can be incorporated in the compounds of the invention in the order written above or in the reverse order. For example, a suitable "A" substituent is C$_{0-8}$alkyl-O—C$_{0-8}$alkyl-CO—NR$^5$-C$_{0-8}$alkyl. It is understood that the "Z" substituent can be positioned to the right or to the left of this sequence.

Preferred "Y" substituents are —COOH and —COOR$^4$, more preferably —COOH. R$^4$ is preferably C$_{1-10}$alkyl.

Preferred "A" substituents are selected from the group consisting of C$_{0-8}$alkyl-NR$^5$—CO—C$_{0-8}$alkyl, C$_{0-8}$alkyl-CO—NR$^5$—C$_{0-8}$alkyl, C$_{1-8}$alkyl-NR$^5$—CO—C$_{1-8}$alkyl-NR$^5$—CO—C$_{0-8}$alkyl, C$_{0-8}$alkyl-NR$^5$—CO—C$_{0-8}$alkyl-CO—NR$^5$-C$_{0-8}$alkyl, C$_{1-8}$alkyl-CO—NR$^5$-C$_{1-8}$alkyl-NR$^5$—CO—C$_{0-8}$alkyl, C$_{0-8}$alkyl-CO—NR$^5$—C$_{0-8}$alkyl-CO—NR$^5$—C$_{0-8}$alkyl, C$_{0-8}$alkyl-CO—C$_{1-8}$alkyl-CO—NR$^5$-C$_{0-8}$alkyl, C$_{0-8}$alkyl-O—C$_{2-8}$alkyl-NR$^5$—CO—C$_{0-8}$alkyl, C$_{0-8}$alkyl-O—C$_{0-8}$alkyl-CO—NR$^5$-C$_{0-8}$alkyl, C$_{0-8}$alkyl-O—C$_{2-8}$alkyl-O—C$_{0-8}$alkyl-CO—NR$^5$—C$_{0-8}$alkyl, C$_{0-8}$alkyl-S—C$_{2-8}$alkyl-NR$^5$—CO—C$_{0-8}$alkyl, C$_{0-8}$alkyl-S(O$_n$)-C$_{2-8}$alkyl-NR$^5$—CO—C$_{0-8}$alkyl, C$_{0-8}$alkyl-S—C$_{0-8}$alkyl-CO—NR$^5$—C$_{0-8}$alkyl, C$_{0-8}$alkyl-S(O$_n$)-C$_{1-8}$alkyl-CO—NR$^5$—C$_{0-8}$alkyl, C$_{0-8}$alkyl-NR$^5$—CO—C$_{0-8}$alkyl-S—C$_{0-8}$alkyl, C$_{0-8}$alkyl-NR$^5$—CO—C$_{1-8}$alkyl-S(O$_n$)—C$_{0-8}$alkyl, C$_{0-8}$alkyl-CO—NR$^5$-C$_{2-8}$alkyl-S—C$_{0-8}$alkyl, C$_{0-8}$alkyl-CO-NR$^5$-C$_{2-8}$alkyl-S(O$_n$)-C$_{0-8}$alkyl, C$_{0-8}$alkyl-NR$^5$-C$_{0-8}$alkyl-CO$_2$—C$_{0-8}$alkyl, C$_{0-8}$alkyl-NR$^5$-C$_{0-8}$alkyl-CS—O—C$_{0-8}$alkyl, C$_{0-8}$alkyl-NR$^5$-C$_{0-8}$alkyl-CO—NR—C$_{0-8}$alkyl, C$_{0-8}$alkyl-NR$^5$-C$_{0-8}$alkyl-CS—NR$^5$-C$_{0-8}$alkyl, C$_{0-8}$alkyl-O—C$_{0-8}$alkyl-CO$_2$—C$_{0-8}$alkyl, C$_{0-8}$alkyl-O—C$_{0-8}$alkyl-CS—C$_{0-8}$alkyl; C$_{0-8}$alkyl-SiR$^7$R$^8$-C$_{0-8}$alkyl, C$_{0-8}$alkyl-SiR$^7$R$^8$-C$_{0-8}$alkyl-NR$^6$—CO—C$_{0-8}$alkyl and C$_{0-8}$alkyl-SiR$^7$R$^8$-C$_{0-8}$alkyl-CO—NR$^6$—C$_{0-8}$alkyl.

More preferred "A" substituents are selected from the group consisting of C$_{0-8}$alkyl-CO—NR$^5$—C$_{0-8}$alkyl, C$_{0-8}$alkyl-O—C$_{0-8}$alkyl-CO—NR$^5$—C$_{0-8}$alkyl, C$_{0-8}$alkyl-O—C$_{2-8}$alkyl-O—C$_{0-8}$alkyl-CO—NR$^5$—C$_{0-8}$alkyl, C$_{0-8}$alkyl-S—C$_{0-8}$alkyl-CO—NR$^5$—C$_{0-8}$alkyl, C$_{0-8}$alkyl-S(O$_n$)-C$_{1-8}$alkyl-CO—NR$^5$—C$_{0-8}$alkyl, C$_{0-8}$alkyl-NR$^5$—CO—C$_{0-8}$alkyl-S—C$_{0-8}$alkyl, C$_{0-8}$alkyl-NR$^5$—CO—C$_{1-8}$alkyl-S(O$_n$)—C$_{0-8}$alkyl, C$_{0-8}$alkyl-NR$^5$—C$_{0-8}$alkyl-CO$_2$—C$_{0-8}$alkyl, C$_{0-8}$alkyl-NR$^5$—C$_{0-8}$alkyl-CO—NR$^5$—C$_{0-8}$alkyl, C$_{0-8}$alkyl-O—C$_{0-8}$alkyl-CO$_2$-C$_{0-8}$alkyl.

Preferably, "Z" is —NH—C(NR$^9$R$^{10}$)=NR$^{11}$. Preferably R$^9$, R$^{10}$ and R$^{11}$ are independently selected from the group consisting of H and C$_{1-6}$alkyl. More preferably, R$^9$, R$^{10}$ and R$^{11}$ are H.

Preferred R$^2$ substituents are —SO$_2$-aryl and —SO$_2$—C$_{1-10}$alkyl. More preferably, R$^2$ is —SO$_2$-aryl.

Preferred R$^3$ substituents are H and C$_{1-8}$alkyl. More preferably, R$^3$ is H.

Preferred compounds and subgroups of compounds may be selected from any combination of the formulas presented in this specification with one or more of the preferred groupings of substituents at a particular location.

Other preferred compounds of the present invention are shown but not limited to the following list of compounds which have the structure:

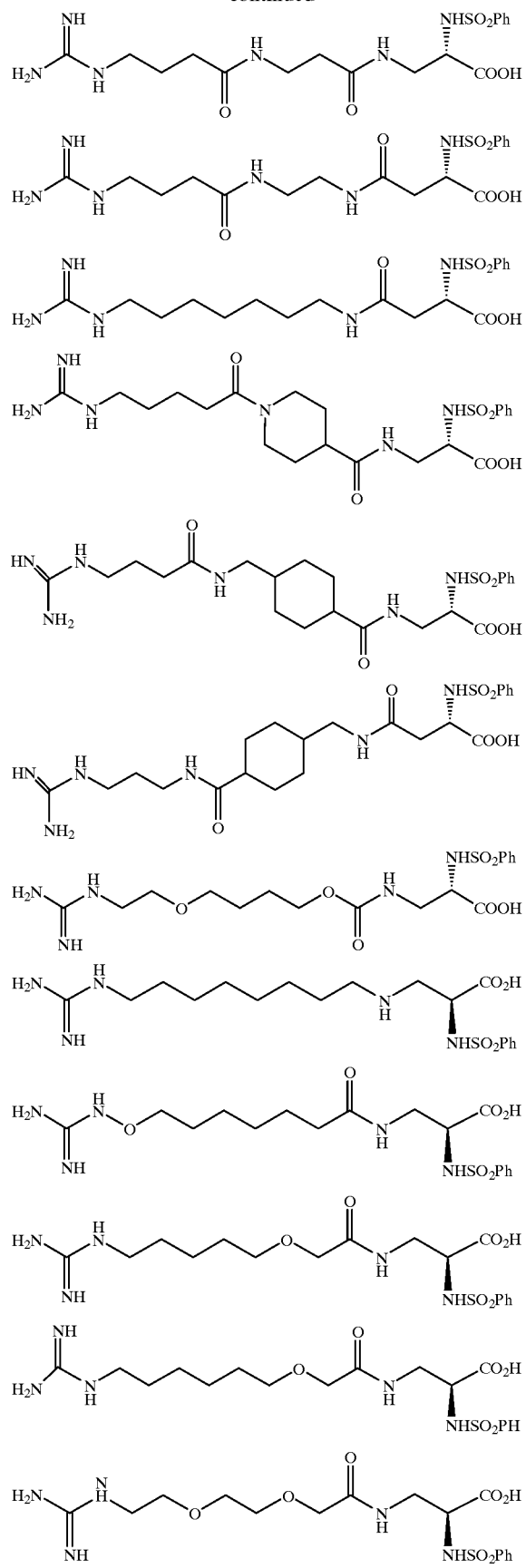
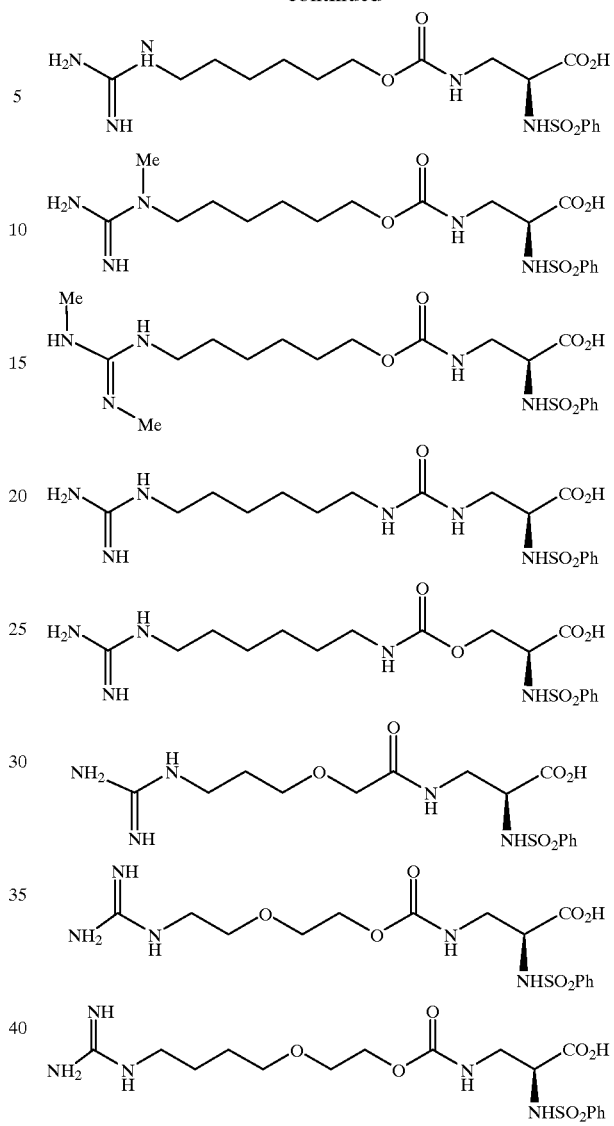

This invention also encompasses prodrug derivatives of the compounds contained herein. The term "prodrug" refers to a pharmacologically-inactive derivative of a parent drug molecule that requires biotransformation, either spontaneous or enzymatic, within the organism to release the active drug. Prodrugs are variations or derivatives of the compounds of this invention which have metabolically cleavable groups and become, by solvolysis under physiological conditions, or by enzymatic degradation, compounds which are pharmaceutically active in vivo. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, H., *Design of Prodruqs,* pp. 7–9, 21–24, Elsevier, Amsterdam 1985 and Silverman, R. B., *The Organic Chemistry of Drug Design and Drug Action,* pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Preparation of Compounds

The compounds of the present invention may be synthesized by either solid or liquid phase methods described and referenced in standard textbooks, or by a combination of both methods. These methods are well known in the art. See, Bodanszky, M., in "The Principles of Peptide Synthesis", Hafner, K., Rees, C. W., Trost, B. M., Lehn, J.-M., Schleyer, P. v-R., Zahradnik, R., Eds., Springer-Verlag, Berlin, 1984. Starting materials are commercially available reagents and reactions are carried out in standard laboratory glassware and reaction vessels under reaction conditions of standard temperature and pressure, except where otherwise indicated.

The starting materials used in any of these methods are commercially available from chemical vendors such as Aldrich, Sigma, Nova Biochemicals, Bachem Biosciences, and the like, or may be readily synthesized by known procedures.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, E. & Meienhofer, J., Eds., 1981) and Vol. 9 (, S. &., Eds., 1987), the disclosures of which are incorporated herein by reference.

Nine exemplary synthesis schemes are outlined below, and the specific syntheses are described in the Examples. The reaction products are isolated and purified by conventional methods, typically by solvent extraction into a compatible solvent. The products may be further purified by column chromatography or other appropriate methods.

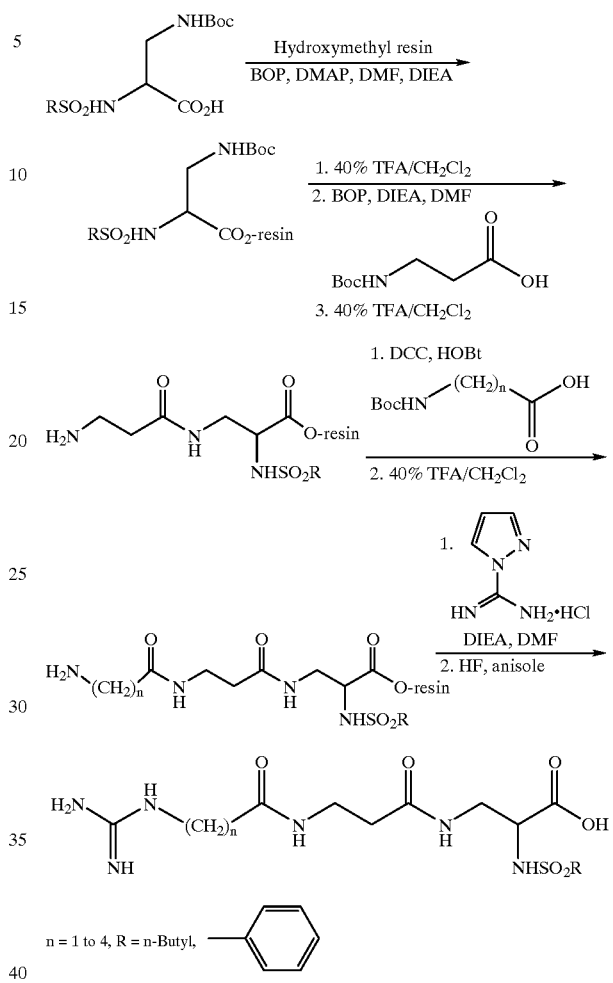

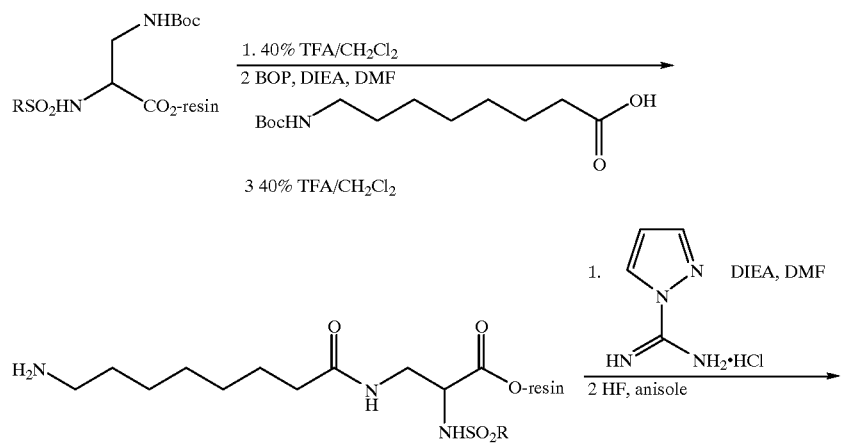

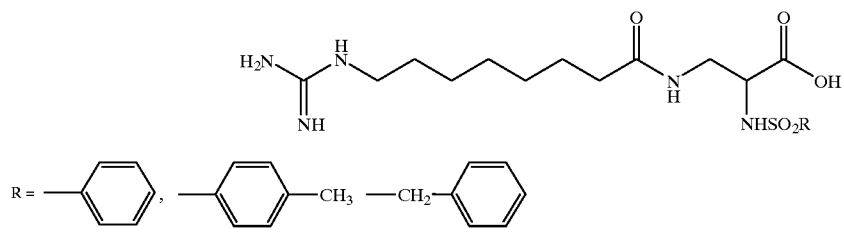
R = phenyl, p-tolyl, –CH₂–phenyl
Scheme 3-A
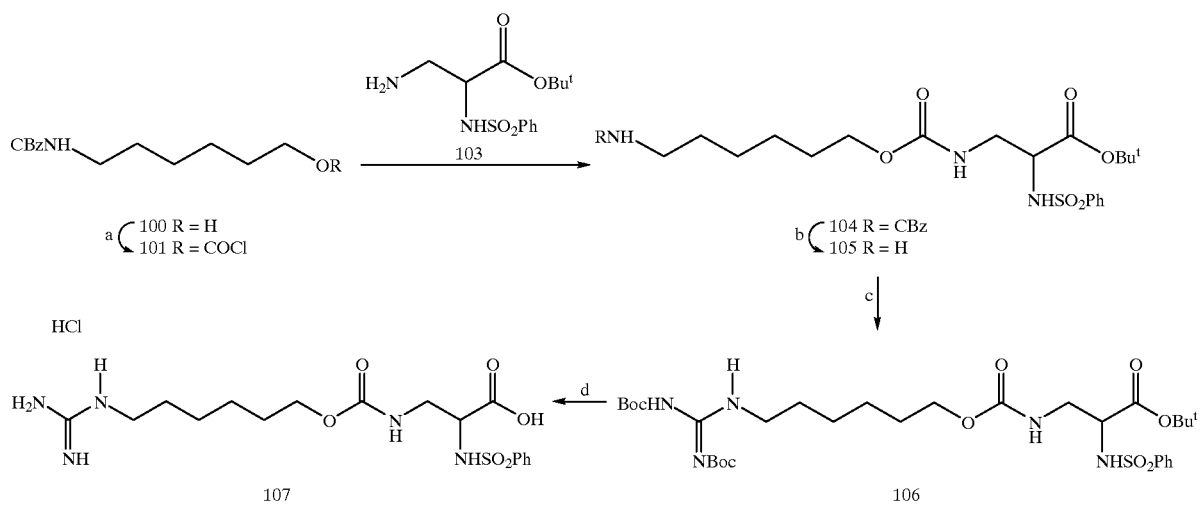
a) Phosgene; b) H₂—Pd/C; c) N,N'-bis(tert-butoxycarbonyl)-S-methoxy-isothiourea; d) TFA-HCl
Scheme 3-B
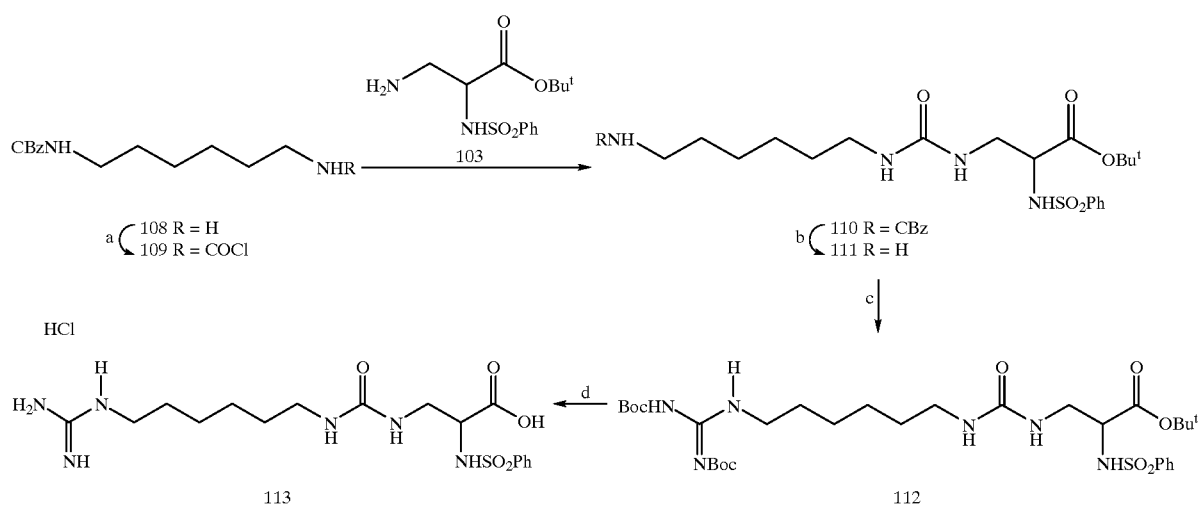
a) Phosgene; b) H₂—Pd/C; c) N,N'-bis(tert-butoxycarbonyl)-S-methoxy-isothiourea; d) TFA-HCl Scheme 3-C

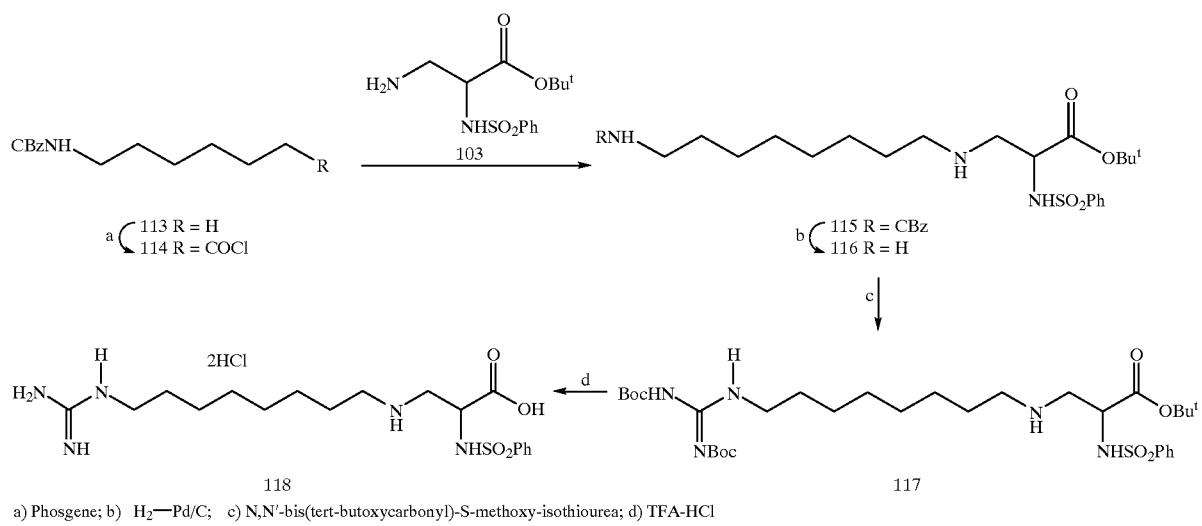

a) Phosgene; b) H₂—Pd/C; c) N,N'-bis(tert-butoxycarbonyl)-S-methoxy-isothiourea; d) TFA-HCl The preparation of the carbamate containing compound 107 typifies the construction of compounds containing this linkage (Scheme 3-A). In the first step, a suitable protected amino alcohol (illustrated with analog 100) is allowed to react with excess phosgene to provide the intermediate chloroformate (101). This material is condensed with the differentially protected diamino propionate derivative 103, thus producing the carbamate linked intermediate (104). The CBz group on the terminal amine is then removed with palladium and hydrogen (105) and the formed amine is reacted with N,N'-bis(tert-butoxycarbonyl)-S-methoxy-isothiourea producing the protected guanidine derivative (106). The compound is completely deprotected with neat TFA at room temperature and then subjected to a salt exchange with HCl providing the desired amino acids (107). Compounds containing a urea linkage (113) are prepared in an analogous manner starting from differentially protected diamines (Scheme 3-B).

Compounds that contain an amine linkage (118) can be prepared in a similar fashion (Scheme 3-A). Protected bromo-amine 114 (prepared from alcohol 113 by treatment with CBr₄ and Ph₃P) is allowed to react with amine 103 in the presence of K₂CO₃ which forms adduct 115. Subjection of protected derivative 115 to the same sequence of reactions outlined for the transformation of 104 into 107 affords the desired amine containing compound 118.

Compositions and Formulations

The compounds of this invention may be isolated as the free acid or base or converted to salts of various inorganic and organic acids and bases. Such salts are within the scope of this invention. Non-toxic and physiologically-compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences,* Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, inhibitors of this invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically-effective dosages may be determined by either in vitro or in vivo methods. For each particular compound of the present invention, individual determinations may be made to determine the optimal dosage required. The range of therapeutically-effective dosages will naturally be influenced by the route of administration, the therapeutic objectives, and the condition of the patient. For injection by hypodermic needle, it may be assumed the dosage is delivered into the bodys fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically-acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone, or in combination with other therapeutic or diagnostic agents. In certain preferred embodiments, the compounds of this invention may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, (e.g. humans), sheep, horses, cattle, pigs, dogs, cats, rats and mice, or in vitro.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

The compounds of the present invention preferably have an $IC_{50}$ of less than about 2.0 $\mu$M, more preferably less than about 1.0 μM, and most preferably less than about 200 nM, as measured by one or more of the assays described herein. These compounds, selected and used as disclosed herein, are believed to be useful for preventing or treating a condition characterized by undesired thrombosis, such as, by way of illustration and not limitation, (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) coagulopathy and disseminated intravascular coagulation (g) the treatment or prevention of thrombotic complications associated with instrumentation (e.g. cardiac or other intravascular catheterization, intra-aortic balloon pump, coronary stent or cardiac valve), (h) those involved with the fitting of prosthetic devices, (i) vascularization of solid tumors and (j) retinopathy.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

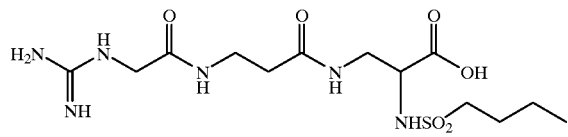
(4)

Part A: Synthesis of 2-(n-Butylsulfonylamido)-3-(N-Boc)-aminopropionic acid hydroxymethyl resin (1)

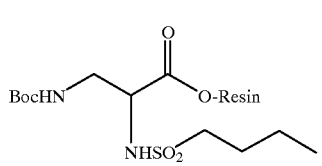
(1)

Hydroxymethyl resin (2.7 g, 2.1 mmol, 0.8 mmol/ g) was suspended in DMF (20 ml). 2-(n-Butylsulfonylamido)-3-(N-Boc)-aminopropionic acid ( prepared according to Claremon, D. A., et al., PCT/US94/01881) (1.0 g, 3.0 mmol), BOP (2.8 g, 6.3 mmol), DIEA (2.0 ml, 11.1 mmol) and catalytic amount of DMAP were added. The mixture was rotated on a nutator at r.t. overnight. The resulting resin (1) was collected in a fritted glass Buchner funnel, washed with MeOH, $CH_2Cl_2$ and dried in vacuo.

Part B:

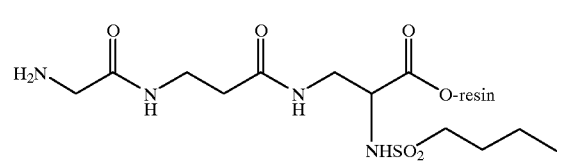
(2)

Compound (2) was synthesized by standard automated solid-phase synthesis protocols using an Applied Biosystems 431 A Peptide Synthesizer. The resin (1) was deprotected with 50% $TFA/CH_2Cl_2$ followed by coupling with N-Boc-β-alanine. The Boc group was removed again with 50% $TFA/CH_2Cl_2$ followed by coupling with N-Boc-glycine. The Boc group was removed with TFA and the resin dried.

Part C:

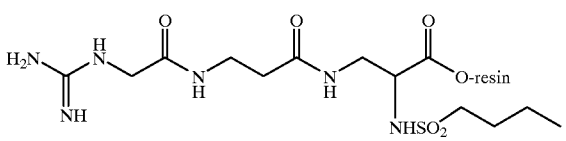
(3)

The resin (2) (0.5 mmol of peptide theoretical) was neutralized with 10% $DIEA/CH_2Cl_2$ and swelled and saturated with DMF (15 ml). 1H-Pyrazole-1-carboxamidine hydrochloride (2 g, 13.8 mmol) and DIEA (2.9 ml, 15.7 mmol) were added to the resin mixture. The reaction was allowed to proceed at 37° for 2 hr. after which the Kaiser ninhydrin test of a resin sample was negative. The resulting resin was washed with $CH_2Cl_2$ and $CH_3OH$ and dried in vacuo.

Part D: HF Cleavage of the resin (3).

The resin (3) (1 g) was suspended in HF (10 ml/g resin) containing 10% by volume anisole and 2% methylethylsulfide (MES) employing a type 1B HF cleavage apparatus. The liquid HF was condensed into the cleavage vessel with the aid of liquid nitrogen cooling and was then maintained at −10° C. for 30 min. and at 0° C. for an additional 30 min. The HF was removed in vacuo and the resin transferred to a fritted glass funnel. The resin was washed with ether followed by extraction of the crude product from the resin with 2N aqueous acetic acid. Lyophilization of the extracts furnished a white powder. The product (4) was purified by preparative HPLC. MS (ES) 395 (M+H⁺)

Example 2

(5)

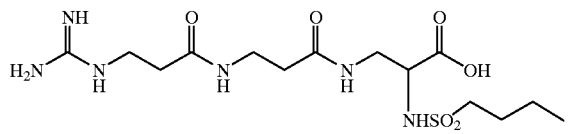

Compound (5) was synthesized by the method of Example 1 using N-Boc-β-alanine in place of N-Boc-glycine in Part B. MS (ES) 409 (M+H⁺)

Example 3

(6)

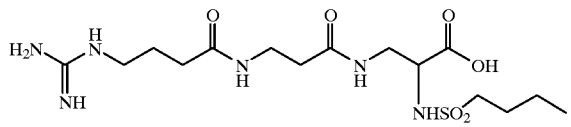

Compound (6) was synthesized by the method of Example 1 using N-Boc-4-aminobutyric acid in place of N-Boc-glycine in Part B. MS (ES) 423 (M+H⁺)

Example 4

(7)

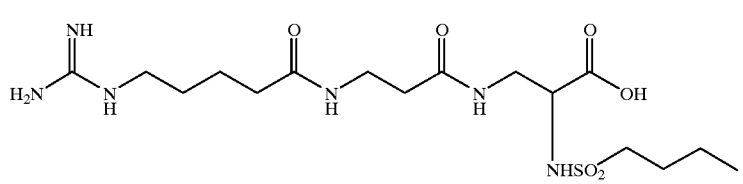

Compound (7) was synthesized by the method of Example 1 using N-Boc-5-aminovaleric acid in place of N-Boc-glycine in Part B. MS (ES) 437 (M+H⁺)

Example 5

(8)

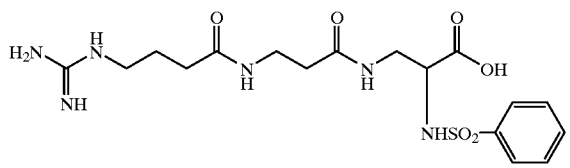

Compound (8) was synthesized by the method of Example 1 using 2-(benzenesulfonylamido)-3-(N-Boc)-aminopropionic acid (prepared as described by Claremon, D. A., et al., PCT/US94/01881, the disclosure of which is incorporated herein by reference) in place of 2-(n-butylsulfonylamido)-3-(N-Boc)-aminopropionic acid. MS (ES) 443 (M+H⁺)

Example 6

(9)

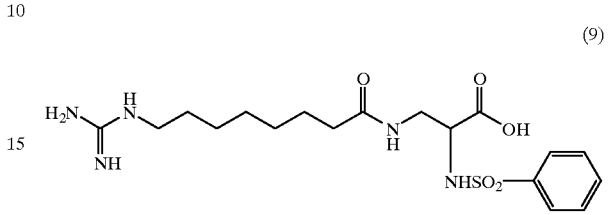

PART A:

(10)

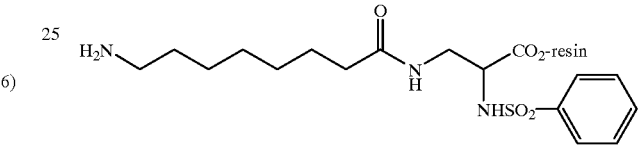

To the 2-(benzenesulfonylamido)-3-(N-Boc)-aminopropionic acid hydroxymethyl resin from Example 5 (0.75 g, 0.375 mmol) in a fritted reaction vessel, was added 40% TFA/CH₂Cl₂. The mixture was stirred at r.t. for 30 min. The resulting 2-(benzenesulfonylamido)-3-aminopropionic acid hydroxymethyl resin was collected through filtration, washed with CH₂Cl₂ and MeOH repeatedly and neutralized with 10% DIEA in CH₂Cl₂. Then, a solution of 8-(N-Boc) aminooctanoic acid (0.195 g, 0.75 mmol), BOP (0.5 g, 1.1 mmol) and DIEA (0.35 ml, 1.9 mmol) in 2 ml of DMF was added to the neutralized resin. The reaction proceeded on a nutator at r.t. for 8 hr., after which the Kaiser ninhydrin test of a resin sample was negative. The mixture was filtered and the resin collected. The resin was washed with CH₂Cl₂, MeOH, dried in vacuo and the Boc group cleaved with 40% TFA/CH₂Cl₂. The resulting free amino-containing resin was washed and dried in vacuo to yield titled compound (10).

Part B:

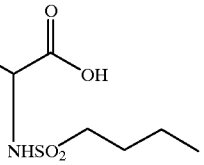

Compound (9) was synthesized by the method of Part C and D of Example 1 using (10) in place of (2) in Part B. MS (ES) 428 (M+H⁺)

Example 7

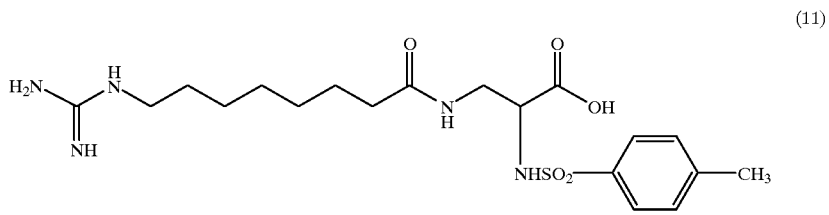
(11)

Compound (11) was synthesized by the method of Example 6 using p-toluenesulfonyl chloride in place of benzenesulfonyl chloride. MS (ES) 442 (M+H$^+$)

Example 8

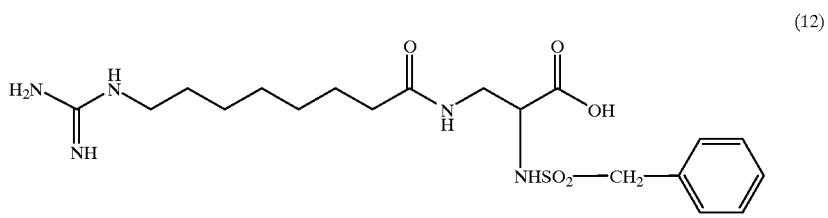
(12)

Compound (12) was synthesized by the method of Example 6 using α-toluenesulfonyl chloride in place of benzenesulfonyl chloride. MS (ES) 442 (M+H$^+$)

Example 9

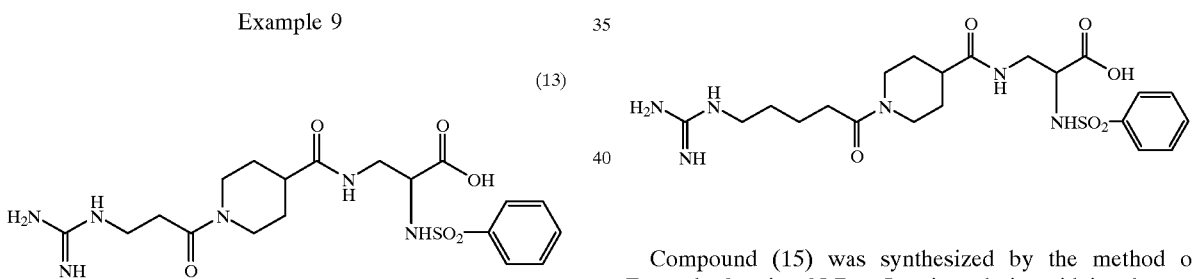
(13)

Compound (13) was synthesized by the method of Part B, C, and D of Example 1 using N-Boc-β-alanine, N-Boc-isonipecotic acid and 2-(benzenesulfonylamido)-3-(N-Boc)-aminopropionic acid hydroxymethyl resin. MS (ES) 469 (M+H$^+$)

Example 10

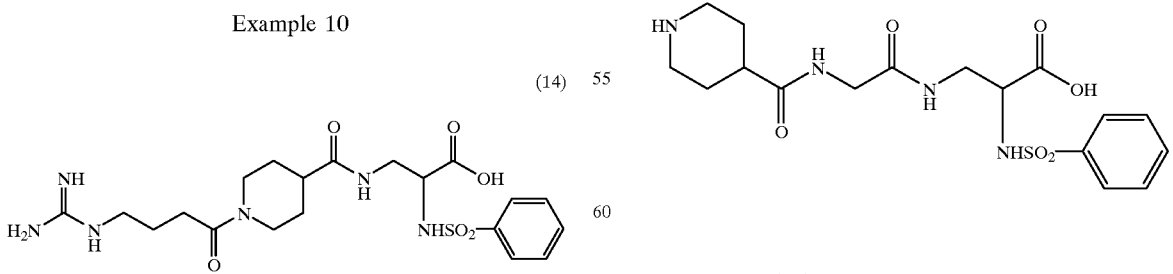
(14)

Compound (14) was synthesized by the method of Example 9 using N-Boc-4-aminobutyric acid in place of N-Boc-β-alanine. MS (ES) 483 (M+H$^+$)

Example 11

(15)

Compound (15) was synthesized by the method of Example 9 using N-Boc-5-aminovaleric acid in place of N-Boc-β-alanine. MS (ES) 497 (M+H$^+$)

Example 12

(16)

Compound (16) was synthesized by the method of Example 9 (omitting the step of guanylating the nitrogen) using N-Boc-isonipecotic acid in place of N-Boc-β-alanine at the N-terminus and N-Boc-glycine in place of N-Boc-isonipecotic acid as the central spacer. MS (ES) 413 (M+H$^+$)

Example 13

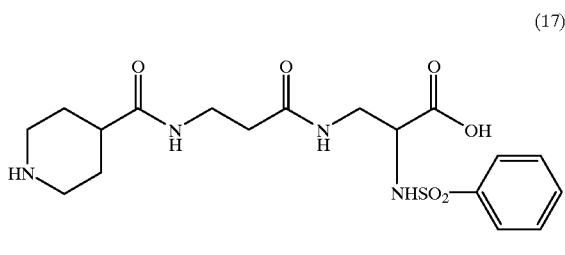

(17)

Compound (17) was synthesized by the method of Example 12 using N-Boc-β-alanine in place of N-Boc-glycine. MS (ES) 427 (M+H$^+$)

Example 14

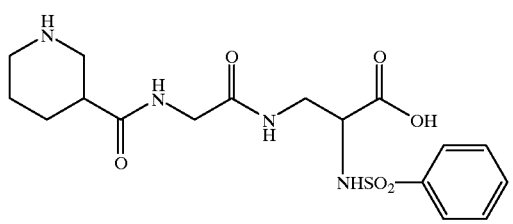

(18)

Compound (18) was synthesized by the method of Example 12 using N-Boc-nipecotic acid in place of N-Boc-isonipecotic acid. MS (ES) 413 (M+H$^+$)

Example 15

Part A:

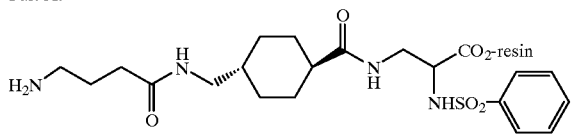

(19)

Compound (19) was synthesized by the method of Part A of Example 6 using trans-(Boc-4-aminomethyl)-cyclohexanecarboxylic acid and N-Boc-4-aminobutyric acid in place of 8-(N-Boc)aminooctanoic acid and using HBTU in place of BOP.

Part B:

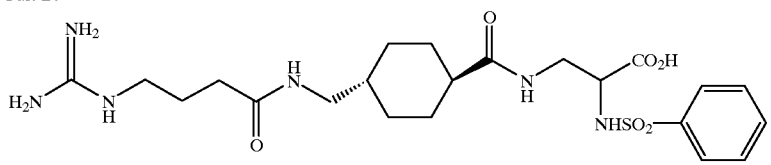

(20)

Compound (20) was synthesized from compound (19) by the method of part C and D of Example 1. MS (ES) 511 (M+H)$^+$

Example 16

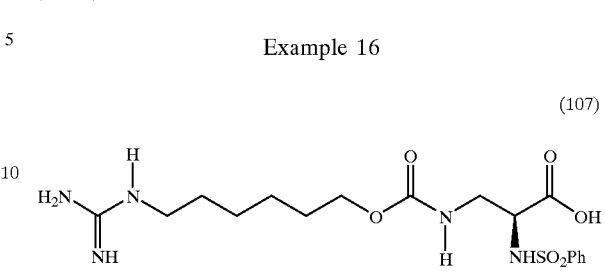

(107)

Preparation of 107 (Scheme 3-A)

Step 1.

A mixture of CBz protected amino-hexanol 100 (0.10 g, 0.39 mmol) was dissolved in toluene (5 mL) and treated with a 2M solution of phosgene in toluene (2 mL). This solution was allowed to stir for 2 h at room temperature and was then concentrated to dryness. The residue was then dissolved in CH$_2$Cl$_2$ (5 mL) and added to a solution of 103 (0.0.12 g, 0.39 mmol), pyridine (1 mL) and CH$_2$Cl$_2$ (5 mL). The resulting solution was allowed to stir for 2 h. The solution was then diluted with EtOAc (100 mL) and washed with saturated NaHCO$_3$ and water. The organic material was then dried (MgSO$_4$) an concentrated. The crude residue was purified by chromatography (silica gel, Hexanes-EtOAc 1:1) giving 0.213 g of 104.

Step 2.

A mixture of compound 104 (0.213 g), 10% palladium on carbon (0.2g), and ethanol (10 mL) was stirred under an atmosphere of hydrogen for 2h and then filtered and concentrated providing 0.14 g of the desired amine 105.

Step 3.

A mixture of the amine 105 (0.14 g, 0.32 mmol), N,N'-bis(tert-butoxycarbonyl)-S-methoxy-isothiourea (0.147 g, 0.49 mmol), and CH$_2$Cl$_2$ (1 mL) was maintained at room temperature for 48 h and then was concentrated. This material was then purified by chromatography (silica gel, hexanes-EtOAc - 1:1) providing 106.

Step 4.

A mixture of the 106 (0.1 g) was dissolved in anhydrous TFA (5 mL) and maintained at room temperature for 1 h. This material was then concentrated to dryness and the resulting material was taken up in 2N HCl (5 mL) and lyophilized providing 107 as a white hygroscopic solid. MS (m/e) 430 (MH+).

Example 17

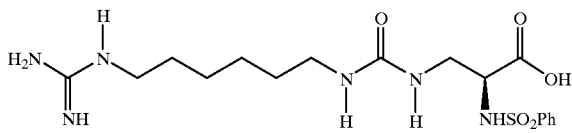
(113)

Preparation of 113 (Scheme 3-B)

Mono CBz protected hexane diamine (108) was converted to the urea derivative 110 following the same procedure employed for the preparation of 104 (Example 16 step 1). Compound 104 was further transformed by first removing the CBz protecting group using the procedure outlined in Example 16 step 2 which afforded amine 111. This material was converted to the protected guanidine 112 using the procedure outlined in Example 16 step 3. . Finally the desired material (113) was obtained using the procedure outlined in Example 16 step 4. . MS (m/e) 428 (MH+).

A mixture of the bromide 114 (0.11 g, 0.33 mmol), amine 103 (0.10 g, 0.33 mmol), and K2CO3 (0.05 g, 0.33 mmol) in CH$_3$CN (1 mL) was stirred at 50° C. overnight. The mixture was then diluted with EtOAc (50 mL) and washed with H$_2$O. The organic material was dried and concentrated. Chromatography (silica gel - EtOAc) gave 0.05 g of 115 as a clear oil. Compound 115 was further transformed by first removing the CBz protecting group using the procedure outlined in Example 16 step 2 which afforded amine 116. This material was converted to the protected guanidine 117 using the procedure outlined in Example 16 step 3. Finally the desired material (118) was obtained using the procedure outlined in Example 16 step 4. MS (m/e) 414 (MH+).

Scheme 4

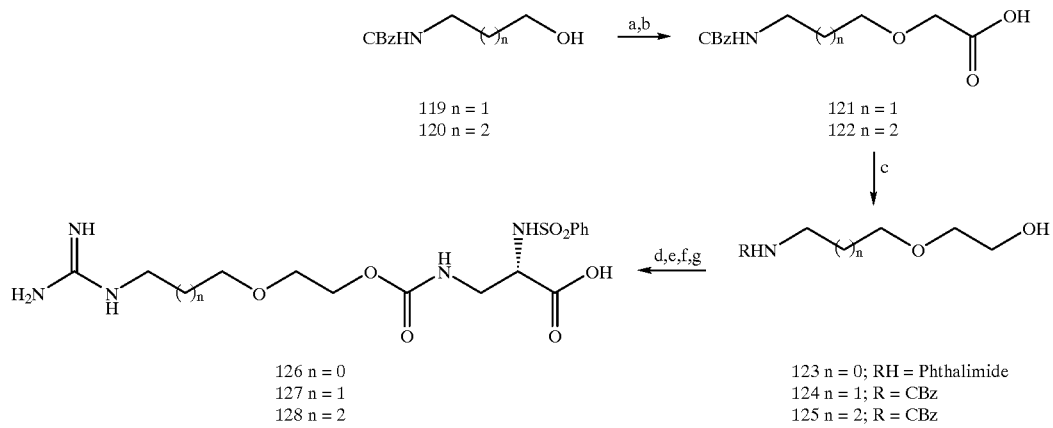

a) EtO$_2$CCHN$_2$, Rh(OAc)$_2$ b) LiOH, EtOH c) N-methyl morpholine, EtO$_2$CCl, NaBH$_4$
d) Phosgene, then 103 e) H$_2$NNH$_2$ for 126, H$_2$ Pd/C for 127 and 128 f) N,N'-bis(tert-butoxycarbonyl)-S-methoxy-isothiourea g) TFA

Example 18

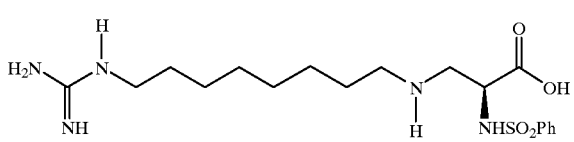
(118)

Preparation of 118 (Scheme 3-C)

Example 19

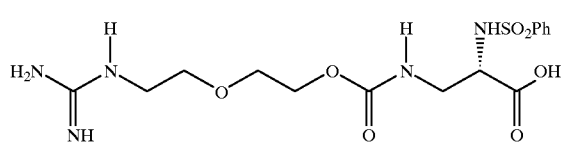
(126)

Preparation of 126 (Scheme 4)

2-2-Phthaloylethoxy)ethanol 123 (200mg, 0.85 mmol) [prepared under standard conditions from 2-(2-aminoethoxy)ethanol and phthalic anhydride] was treated with phosgene (2.2 mL, 1.93M in toluene, 4.3 mmol). After 1 h, the mixture was concentrated and the residue dissolved in pyridine (2 mL). This mixture was then added dropwise to a solution of amine 103 (255 mg, 0.85 mmol) in pyridine (2 mL). After 1 h, the mixture was poured into H$_2$O and ethyl acetate (EtOAc). The layers were separated, the aqueous layer washed with EtOAc (2×), and the combined extracts were dried (MgSO$_4$) and concentrated. The residue was purified by chromatography (SiO$_2$, 1:1 hexane:EtOAc) affording 180 mg (32%) of the desired carbamate. Deprotection of the phthalimide was accomplished by treatment of the carbamate product with hydrazine hydrate (0.80 mL) in ethanol (2 mL). After 1 h, the mixture was concentrated, partitioned between NaHCO$_3$(aq) and EtOAc, and the layers were separated. The organic extract was washed with NaHCO$_3$(aq)(2×), dried (MgSO$_4$), and concentrated yielding 66 mg (48%) of the corresponding amine. The protected guanidine was prepared according to a similar procedure described for the preparation of 107 (Scheme 1). Deprotection with trifluoroacetic acid (TFA) yielded the TFA salt of the desired product 126. MS (m/e) 418 (MH+).

Example 20

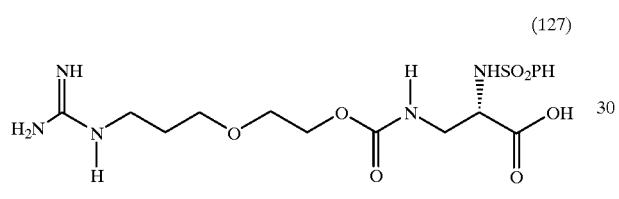

(127)

Preparation of 127 (Scheme 4)

Step 1.

A solution of CBz protected 3-aminopropanol 119 (500 mg, 0.24 mmol) and rhodium(II) acetate dimer (10 mg) in CH$_2$Cl$_2$ (40 mL) was treated dropwise with a CH$_2$Cl$_2$ solution of ethyl diazoacetate (0.28 mL, 2.63 mmol). After 1 h, the mixture was concentrated and the residue was purified by flash chromatography (SiO$_2$, 1:1 hexane:EtOAc) affording 560 mg (79 %) of the ethyl ester. The ester (300 mg) was dissolved in EtOH (10 mL) and treated with NaOH (203 mg, 0.51 mmol). After 1 h, the mixture was concentrated and the residue dissolved in H$_2$O. The pH was adjusted to ~2–3 using 1N HCl and then EtOAc was added and the layers were separated. The aqueous layer was washed with EtOAc (2×), the combined extracts were then dried (MgSO$_4$) and concentrated yielding 227 mg (83%) of acid 121.

Step 2.

A solution of acid 121 (227 mg, 0.085 mmol) and N-methyl morpholine (0.94 mL, 0.085 mmol) in THF (4.5 mL) at −10 C. was treated with ethyl chloroformate (0.82 mL, 0.085 mmol). After 0.25 h, the mixture was treated with sodium borohydride (96 mg, 0.26 mmol) followed by dropwise addition of methanol (9 mL). The mixture was allowed to warm, treated with 10% acetic acid (aq), and concentrated. The residue was partitioned between 1N NaOH and EtOAc, the layers were seperated, the aqueous was washed with EtOAc (2×) and the combined extracts were dried (MgSO4) and concentrated. The residue was purified by chromatography (SiO2, 65:35 EtOAc:hexane) yielding 75 mg (35%) of alcohol 124.

Step 3.

The carbamate derivative 127 was prepared following the same procedures described for the preparation of 107 (Scheme 1). Alcohol 124 (75 mg) was treated with phosgene followed by amine 103 (89 mg) yielding the carbamate (63 mg). Deprotection of the CBz by hydrogenolysis and subsequent treatment of the resulting amine (50 mg) with N,N'-bis(tert-butoxycarbonyl)-S-methoxy-isothiourea (35 mg) yielded the protected guanidine (30 mg). Deprotection with trifluoroacetic acid yielded the TFA salt of the desired product 127. MS (m/e) 432 (MH+).

Example 21

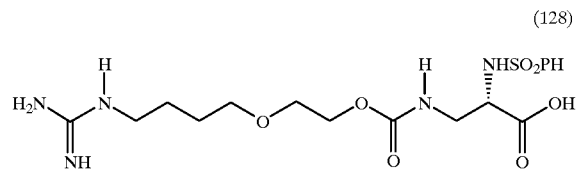

(128)

Preparation of 128 (Scheme 4)

The product 128 was prepared following the same general procedures described for the preparation of 127. CBz protected 4-aminobutanol (1.0 g) was treated with rhodium(II) acetate dimer (10 mg) and ethyl diazoacetate (0.52 mL) yielding the homologated ester (440 mg). Saponification of the ester (728 mg) with NaOH (470 mg) and reduction of the resulting acid 122 (590 mg) with ethyl chloroformate (0.20 mL), N-methyl morpholine (0.23 mL) and sodium borohydride (238 mg) yielded alcohol 125 (134 mg). Treatment of 125 with phosgene followed by amine 103 (151 mg) yielded the desired carbamate (127 mg). Deprotection of the CBz by hydrogenolysis and subsequent treatment of the resulting amine (42 mg) with N,N'-bis(tert-butoxycarbonyl)-S-methoxy-isothiourea (30 mg) yielded the protected guanidine (23 mg). Deprotection with trifluoroacetic acid yielded the TFA salt of the desired product 128. MS (m/e) 446 (MH+).

Scheme 5

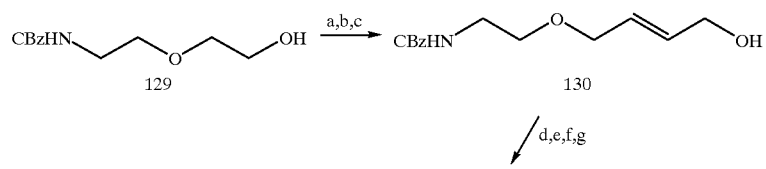

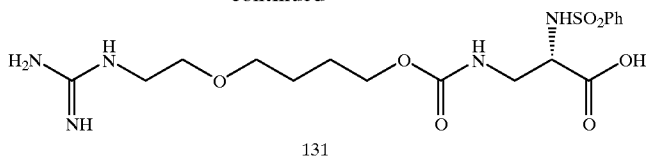

131 a) (COCl)₂, DMSO, Et₃N  b) EtO₂CCH=PPh₃  c) Dibal-H  d) Phosgene, then 103
e) H₂, Pd/C  f) N,N'-bis(tert-butoxycarbonyl)-S-methoxy-isothiourea  g) TFA Example 22

(131)

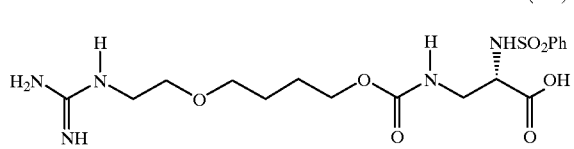

Preparation of 131 (Scheme 5)
Step 1.

A solution of oxalyl chloride (0.99 mL, 11.3 mmol) in CH2Cl2 (40 mL) at −78 C. was treated with dimethyl sulfoxide (0.86 mL, 12.2 mmol). After 0.5 h, a solution of alcohol 129 (1.94 g, 8.12 mmol) in CH2Cl2 (7 mL) was added dropwise. After 0.5 h, triethylamine (2.05 g, 20.3 mmol) was added and the cooling bath was removed. After 1 h, the mixture was poured into EtOAc and NH₄Cl(aq). The layers were separated, the aqueous layer was washed with EtOAc and the combined extracts were dried (MgSO₄). Concentration yielded the corresponding aldehyde. A solution of this crude aldehyde in THF (20 mL) was then treated with (carbethoxymethylene)triphenylphosphorane (2.96 g, 8.50 mmol). After 62 h, the mixture was concentrated and the residue purified by chromatography (SiO₂, 4:1 to 3:2 hexane:EtOAc) yielding the acrylate as a mixture of isomers. A sample of the trans isomer (490 mg, 1.60 mmol) in THF (5 mL) at −78 ° C. was treated with diisobutylaluminum hydride (Dibal-H) (5 mL, 1.0M in toluene, 5.0 mmol). After 1.5 h, the mixture was treated with EtOAc (5 mL) followed by a saturated aqueous solution of NH₄Cl (0.4 mL). After 1 h, the mixture was treated with SiO₂ gel (~4 mL), diluted with EtOAc, and filtered through MgSO₄ and Celite. Concentration yielded 237 mg (56%) of the alcohol 130.

Step 2.

The carbamate derivative 131 was prepared following the same procedures described for the preparation of 107 (Scheme 1). Alcohol 130 (237 mg) was treated with phosgene followed by amine 103 (263 mg) yielding the carbamate (368 mg). Deprotection of the CBz by hydrogenolysis and subsequent treatment of the resulting amine (116 mg) with N,N'-bis(tert-butoxycarbonyl)-S-methoxy-isothiourea (147 mg) yielded the protected guanidine (104 mg, 59%). Deprotection with trifluoroacetic acid yielded the TFA salt which upon treatment with aqueous HCl and lyophilization yielded the HCl salt of the desired product 131. MS (m/e) 446 (M+).

Scheme 6

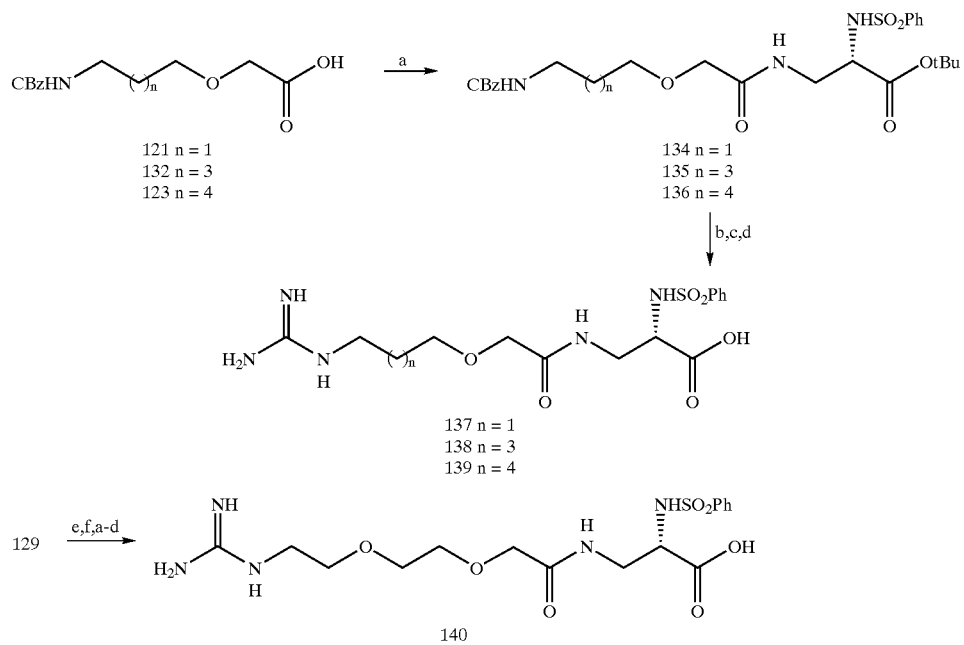

-continued a) 1-[3-(Dimethylamino)propyl]-3-ethylcarbodiimide hydrochloride, 103 b) H₂, Pd/C c) N,N'-bis(tert-butoxycarbonyl)-S-methoxy-isothiourea d) TFA, then HCl e) Rh(OAc)₂, EtO₂CCHN₂ f) NaOH, EtOH Example 23

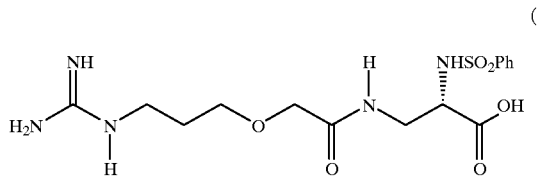

(137)

Preparation of 137 (Scheme 6)

Step 1.

A solution of acid 121 (418 mg, 1.56 mmol) and amine 103 (470 mg, 1.56 mmol) in CH₂Cl₂ (8 mL) was treated with 1-[3-(dimethylamino)propyl]-3-ethylcarbodiimde hydrochloride (EDCl) (300 mg, 1.56 mmol) and triethylamine (0.55 mL, 3.9 mmol). After 2 h, the mixture was concentrated and the residue purified by chromatography (SiO₂, 4:1 EtOAc:hexane) affording 60 mg (7%) of the amide 134.

Step 2.

The amide derivative 137 was then prepared following the same procedures described for 107 (Scheme 3-A, steps 2–4). Hydrogenolysis of 134 (152 mg) yielded the corresponding amine (130 mg). Treatment of the amine (111 mg) with N,N'-bis(tert-butoxycarbonyl)-S-methoxy-isothiourea (85 mg) yielded the protected guanidine (100 mg, 57%). Deprotection with trifluoroacetic acid yielded the TFA salt which upon treatment with aqueous HCl and lyophilization yielded the HCl salt of the desired product 137. MS (m/e) 446 (M+).

Example 24

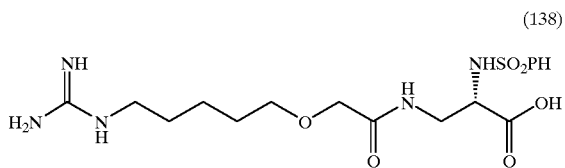

(138)

Preparation of 138 (Scheme 6)

The amide derivative 138 was prepared following the same general procedures described for the preparation of 137 (Scheme 6). Treatment of acid 132 (128 mg, prepared according to the general procedure described for 121, Scheme 4 starting from CBz protected 5-aminopentanol) with amine 103 (130 mg) and EDCl (83 mg) in CH₂Cl₂ yielded amide 135 (140 mg, 56%). Hydrogenolysis of 135 (310 mg) yielded the corresponding amine (226 mg). Treatment of the amine (210 mg) with N,N'-bis(tert-butoxycarbonyl)-S-methoxy-isothiourea (155 mg) yielded the protected guanidine (160 mg, 49%). Deprotection with trifluoroacetic acid yielded the TFA salt which upon treatment with aqueous HCl and lyophilization yielded the HCl salt of the desired product 138. MS (m/e) 430 (M+).

Example 25

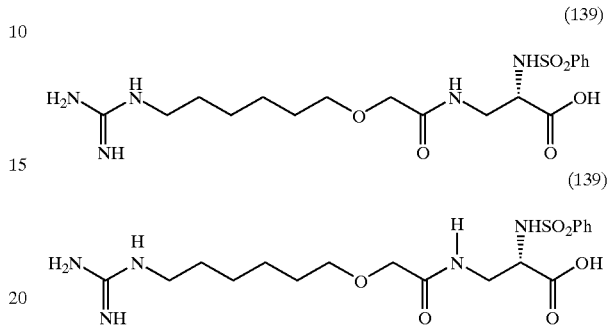

(139)

(139)

Preparation of 139 (Scheme 6)

The amide derivative 139 was prepared following the same general procedures described for the preparation of 137 (Scheme 6). Treatment of acid 133 (200 mg, prepared according to the general procedure described for 121, Scheme 4 starting from CBz protected 6-aminohexanol) with amine 103 (195 mg), EDCl (124 mg), and triethylamine (0.23 mL) in CH₂ Cl₂ yielded amide 136 (169 mg, 44%). Hydrogenolysis of 136 (294 mg) yielded the corresponding amine (141 mg). Treatment of the amine (120 mg) with N,N'-bis(tert-butoxycarbonyl)-S-methoxy-isothiourea (84 mg) yielded the protected guanidine (55 mg, 30%). Deprotection with trifluoroacetic acid yielded the TFA salt which upon treatment with aqueous HCl and lyophilization yielded the HCl salt of the desired product 139. MS (m/e) 444 (M+).

Example 26

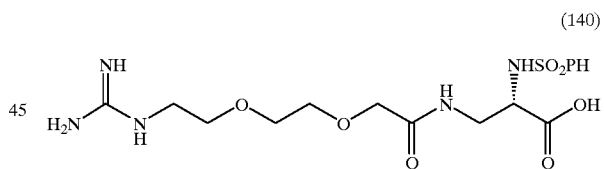

(140)

Preparation of 140 (Scheme 6)

The amide derivative 149 was prepared following the same general procedures described for the preparation of acid 121 (Scheme 4) and amide 137 (Scheme 6). Alcohol 129 (1.45 g, 6.07 mmol) was treated with ethyl diazoacetate (0.70 mL, 6.68 mmol) and rhodium(II) acetate dimer (75 mg) yielding the corresponding ester (993 mg, 50%). Treatment of the ester (525 mg) with sodium hydroxide (324 mg) in EtOH afforded the acid which was then treated with amine 103 (450 mg) and EDCl (311 mg) in CH₂Cl₂ (5 mL) yielding the amide (865 mg, 96%). Hydrogenolysis of the amide (865 mg) yielded the corresponding primary amine (583 mg). Treatment of the amine (355 mg) with N,N'-bis(tert-butoxycarbonyl)-S-methoxy-isothiourea (441 mg) yielded the protected guanidine (68 mg, 11%). Deprotection with trifluoroacetic acid yielded the TFA salt which upon treatment with aqueous HCl and lyophilization yielded the HCl salt of the desired product 139. MS (m/e) 432 (M+).

Scheme 7

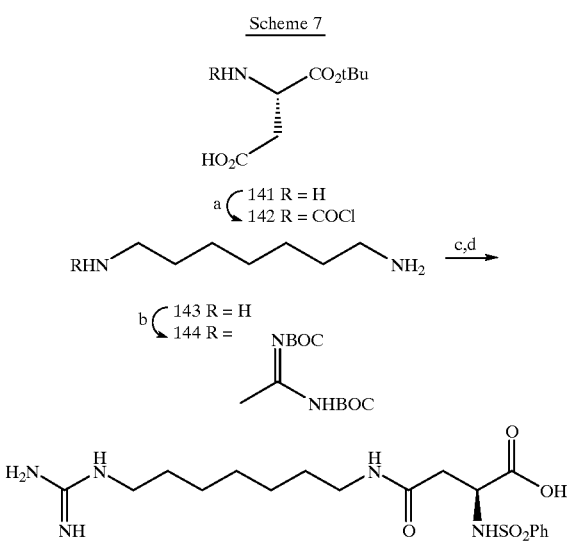

a) PhSO₂Cl, NaOH b) N,N'-bis(tert-butoxycarbonyl)-S-methoxy-isothiourea c) 142,144, 1-[3-(Dimethylamino)propyl]-3-ethylcarbodiimide hydrochloride, Et₃N d) TFA Example 27

(145)

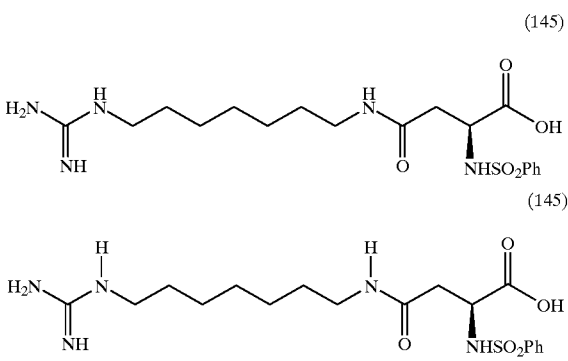

(145)

Preparation of 145 (Scheme 7)

Step 1.

A solution of 141 (5.0 g, 26 mmol) in 1:1 H2O:dioxane (32 mL) at 0 C. was treated with sodium hydroxide (2.14 g, 53 mmol) followed by benzenesulfonyl chloride (3.8 mL, 29 mmol). Upon consumption of 141, the mixture was concentrated and the pH of the mixture was adjusted to ~4 by addition of 1N HCl. The aqueous layer was washed with EtOAc (3×) and the combined extracts were dried (MgSO₄) and concentrated yielding the crude sulfonamide 142 which was used without further purification.

Step 2.

A solution of 1,7-diaminoheptane 143 (3.0 g, 23 mmol) in DMF (10 mL) was treated with N, N'-bis(tert-butoxycarbonyl)-S-methoxy-isothiourea (3.3 g, 12 mmol). The mixture was diluted with H₂O and EtOAc and the layers separated. The aqueous layer was washed with EtOAc (3×) and the combined extracts were washed with 10% citric acid (aq). The aqueous layer was then treated with potassium carbonate until a pH of ~10 was achieved and then washed with EtOAc (3×). The combined extracts were dried (K₂CO₃) and concentrated to yield the crude amine 144 which was used without further purification.

Step 3.

A solution of the crude acid 142 (72 mg) and amine 144 (123 mg) in CH₂Cl₂ was treated with EDCl (42 mg) and triethylamine (0.064 mL). After 16 h, the mixture was concentrated and the residue purified by chromatography (SiO₂, 4:1 to 1:1 hexane:EtOAc) yielding the desired amide (39 mg). Deprotection of the amide with trifluoroacetic acid yielded the TFA salt of the desired product 145. MS (m/e) 428 (MH+).

Example 28

Assay Methods

The identification of compounds which are active platelet aggregation inhibitors is made possible by the observation that compounds which block the binding of fibrinogen to the GPIIb-IIIa complex in vitro are also capable of inhibiting thrombin or. diphosphate (ADP)-induced aggregation of human platelets and the formation of platelet-thrombi in vivo. This observation provides the basis for obtaining potent platelet aggregation inhibitors by evaluating the ability of test materials to disrupt fibrinogen-GPIIb-IIIa interactions. The ability of compounds to inhibit the adhesive function of other integrins that are closely related to GPIIb-IIIa can also be measured in vitro by measuring their ability to inhibit the binding of adhesive ligands to various integrins such as vitronectin receptor ($\alpha_v\beta_3$) and fibronectin receptor ($\alpha_5\beta_1$).

The following assay methods were used to evaluate the compounds of the invention.

Integrin Binding Assays

In the following assays, GPIIb-IIIa and vitronectin receptor, $\alpha_v\beta_3$ were prepared in purified form, by methods described in Fitzgerald, L. A., et al., *Anal Biochem* (1985) 151: 169–177 and Smith, J. W., *J. Biol Chem* (1988) 263: 18726–18731 (the disclosure of which is incorporated herein by reference). GPIIb-IIIa or vitronectin receptor, $\alpha_v\beta_3$, are coated onto microtiter plates. The coated support is then contacted with fibrinogen for the GPIIb-IIIa assay, or is contacted with vitronectin for the vitronectin receptor, $\alpha_v\beta_3$ and with test materials and incubated for sufficient time to reach maximal ligand binding to immobilized integrins. The adhesive ligands fibrinogen or vitronectin were typically provided at a concentration of 2–50 nM and the test material can, if desired, be added at a series of diultions. Typical incubations were 2–4 hr at 25° C., the time and temperature being interdependent.

Description of Purified Integrin Binding Assays

Purified platelet GPIIb-IIIa was prepared by Fitzgerald, L. A., et al., *Anal Biochem* 151:169–177 (1985). Vitronectin receptor, $\alpha_v\beta_3$, was prepared as described by Smith, J. W., *J. Biol Chem* (1988) 263: 18726–18731. After purification, the receptors were each stored in 0.1% Triton X-100 at 0.1–1.0 mg/ml.

The receptors were coated to the wells of 96-well flat-bottom enzyme-linked immunoassay (ELISA) plates (Linbro EIA-Plus microtiter plate, Flow Laboratories) after diluting 1:200 with a solution of 20 mM Tris-HCl, 150 mM NaCl, 1 mM CaCl₂, pH 7.4 to reduce the Triton X-100 concentration to below its critical micellar concentration and adding an aliquot of 100 µl to each well. The wells were allowed to incubate overnight at 4° C., and then aspirated to dryness. Additional sites were blocked by the addition of bovine serum albumin (BSA) at 35 mg/ml in the above buffer for 2 hr at 30° C. to prevent non-specific binding. The wells were then washed once with binding buffer (50 nM Tris-HCl, 100 mM NaCl, 2 mM CaCl₂, 1 mg/ml BSA).

The corresponding ligands (fibrinogen, von Willebrand Factor, or vitronectin) were conjugated to biotin using commercially available reagents and standard protocols. The labeled ligands were added to the receptor-coated wells at a final concentration of 2–10 nM (100 μl/well) and incubated for 3 hr at 25° C. in the presence or absence of test samples. After incubation, the wells were aspirated to dryness and bound ligand containing biotin label was quantitated.

The bound protein was detected by the addition of anti-biotin antibody conjugated to alkaline phosphatase followed by addition of substrate (p-nitrophenyl adenosine phosphate), and determination of the optical density of each well at 405 nM. Decreased color development was observed in wells incubated with test samples which inhibited binding of ligand to receptor. From the various concentrations of test samples, the concentration of inhibitor ($IC_{50}$) which half-maximally inhibits ligand binding was determined The Platelet Aggregation Assay In addition to the ELISA integrin binding assays described above, the Aggregation-Human/PRP/ADP Assay is useful for evaluating therapeutic compounds.

Platelet rich plasma (PRP) is prepared from healthy human volunteers for use in determining inhibition of platelet aggregation by compounds. Blood was collected via a 21 gauge butterfly cannula, using a two-syringe technique into $^1/_{10}$ volume of 105 trisodium citrate.

Platelet rich plasma was prepared at room temperature by centrifugation of the citrated whole blood at 100×g for 15 minutes. The PRP contained approximately 200–400,000 platelets/μl. Platelet poor plasma was prepared by centrifugation of citrated whole blood at 12,000×g for 2 minutes.

Platelet aggregation was assayed in a Chrono-log whole blood aggregometer (Chrono-log Corporation, Havertown, Pa.) using the PRP prepared above according to the manufacturers directions. Inhibition of platelet aggregation was studied by adding varying amounts of test materials followed by adenosine diphosphate (ADP, 20 μM) to stirred human PRP. Specifically, the human PRP was incubated with the compound for 1–2 min. at 37° C. prior to addition of the aggregating agent ADP. From full dose response curves the concentration ($IC_{50}$) to half-maximally inhibit platelet aggregation for test compounds was determined.

TABLE OF ASSAY TEST RESULTS

| Compound # | GPIIbIIIa ELISA ($IC_{50}$ μM) | $α_vβ_3$ ELISA ($IC_{50}$ μM) | PRP ($IC_{50}$ μM) |
|---|---|---|---|
| 4 | >100 | >200 | 120 |
| 5 | 50 | >100 | 67.1 |
| 6 | 0.8 | 0.9 | 4.9 |
| 7 | 1 | 50 | 4.9 |
| 8 | 0.1 | 0.3 | 0.26 |
| 9 | 0.02 | 0.1 | 0.17 |
| 11 | 0.1 | 0.2 | 0.85 |
| 12 | 0.6 | 3.0 | 5.7 |
| 13 | 2.5 | 0.5 | 3.3 |
| 14 | 2.5 | 5.0 | 1.0 |
| 15 | 0.08 | 3.0 | 0.22 |
| 16 | 5.0 | >100 | 49.3 |
| 17 | 0.1 | >100 | 1.1 |
| 18 | 10 | 40 | 122 |
| 20 | 0.075 | 15 | 0.55 |

As can be seen from the compounds listed in the Table of Assay Test Results, a number of compounds of the invention display potent inhibition of ligand binding to GPIIb-IIIa and the vitronectin receptor, $α_vβ_3$, as well as inhibition of ADP-induced human platelet aggregation with $IC_{50}$'s which are submicromolar and would be expected to display anti-integrin activities in vivo.

What is claimed is:

1. A compound having the formula:

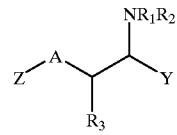

wherein:

Y is selected from the group consisting of —COOH and —COOR$^4$; where R$^4$ is selected from the group consisting of $C_{1-10}$alkyl, $C_{1-8}$alkylaryl, and aryl-$C_{1-8}$alkyl;

A is selected from the group consisting of $C_{0-8}$alkyl-NR$^5$—CO—$C_{0-8}$alkyl, $C_{0-8}$alkyl-CO—NR$^5$—$C_{0-8}$alkyl, $C_{0-8}$alkyl-NR$^5$ —CO—$C_{1-8}$alkyl-NR$^5$—CO—$C_{0-8}$alkyl, $C_{0-8}$alkyl-CO—NR$^5$—$C_{1-8}$alkyl-NR$^5$—CO—$C_{0-8}$alkyl, $C_{0-8}$alkyl-CO—NR$^5$—$C_{0-8}$alkyl-CO—NR$^5$—$C_{0-8}$alkyl, $C_{0-8}$alkyl-CO—$C_{1-8}$alkyl—CO—NR$^5$—$C_{0-8}$alkyl, $C_{0-8}$alkyl-NR$^5$—$C_{0-8}$alkyl-CO—NR$^5$—$C_{0-8}$alkyl, $C_{0-8}$alkyl-O—$C_{0-8}$alkyl-CO—NR$^5$—$C_{0-8}$alkyl, and $C_{0-8}$alkyl-O—$C_{2-8}$alkyl-O—$C_{0-8}$alkyl-CO—NR$^5$—$C_{0-8}$alkyl; where R$^5$ are independently selected from the group consisting of H and $C_{1-6}$alkyl;

Z is selected from the group consisting of —NH—C(NR$^9$R$^{10}$)=NR$^{11}$ and —C(NR$^9$R$^{10}$)=NR; where R$^9$, R$^{10}$ and R$^{11}$ are independently selected from the group consisting of H and $C_{1-6}$alkyl;

R$^1$ is H;

R$^2$ is selected from the group consisting of —SO$_m$-aryl and —SO$_m$—$C_{1-10}$alkyl, where m=2; and R$^3$ is H;

and all pharmaceutically-acceptable stereoisomers, salts, hydrates, solvates and prodrug derivatives thereof.

2. The compound of claim 1 wherein Y is —COOH.

3. The compound of claim 1 wherein R$^2$ is —SO$_2$-aryl.

4. The compound of claim 1 wherein R$^4$ is $C_{1-10}$alkyl.

5. The compound of claim 1 wherein R$^9$, R$^{10}$ and R$^{11}$ are H.

6. The compound of claim 1 wherein Z is —NH—C(NR$^9$R$^{10}$)=NR$^{11}$.

7. The compound of claim 1 wherein A is selected from the group consisting of $C_{0-8}$alkyl-NR$^5$—CO—$C_{0-8}$alkyl, $C_{0-8}$alkyl-NR$^5$—CO—$C_{1-8}$alkyl-NR$^5$—CO—$C_{0-8}$-alkyl, $C_{0-8}$alkyl-CO—$C_{1-8}$alkyl-CO—NR$^5$—$C_{0-8}$alkyl, and $C_{0-8}$alkyl-O—$C_{0-8}$alkyl-CO—NR$^5$-$C_{0-8}$alkyl.

8. The compound of claim 7 wherein Y is —COOH; Z is —NH—C(NR$^9$R$^{10}$)=NR$^{11}$; R$^9$, R$^{10}$ and R$^{11}$ are H; and R$^2$ is —SO$_2$-aryl.

9. The compound of claim 1 wherein A is selected from the group consisting of $C_{0-8}$alkyl-NR$^5$ —CO—$C_{1-8}$alkyl-NR$^5$ —CO—$C_{0-8}$alkyl, and $C_{0-8}$alkyl-O—$C_{0-8}$alkyl-CO—NR$^5$ —$C_{0-8}$alkyl.

10. The compound of claim 9 wherein Y is —COOH; Z is —NH—C(NR$^9$R$^{10}$)=NR$^{11}$; R$^9$, R$^{10}$ and R$^{11}$ are H; and R$^2$ is —SO$_2$-aryl.

11. The compound of claim 1, having an $IC_{50}$ of less than about 200 nM.

12. A compound of claim 1 selected from the group consisting of:

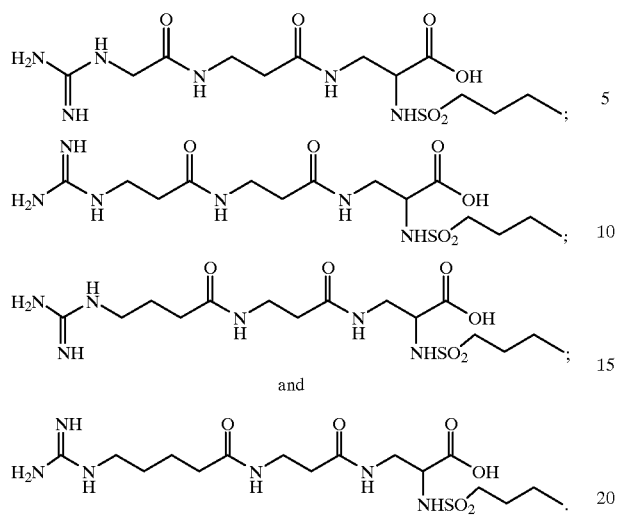

13. A pharmaceutical composition for preventing or treating a condition in a mammal characterized by undesired thrombosis comprising a therapeutically-acceptable carrier and a therapeutically-effective amount of a compound of claim 1.

14. A method for preventing or treating a condition in a mammal characterized by undesired thrombosis comprising administering to said mammal a therapeutically-effective amount of a compound of claim 1.

15. The method of claim 14, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, vascularization of solid tumors and retinopathy.

16. A compound selected from the group consisting of:

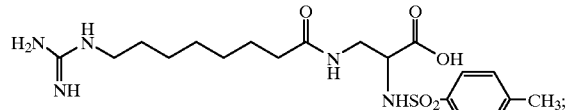

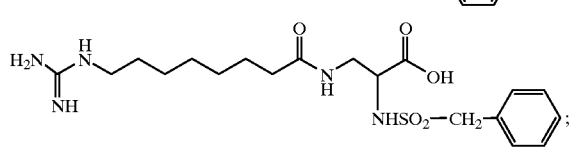

and

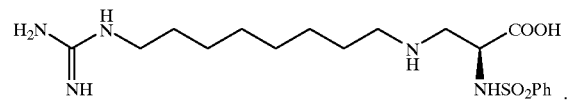

-continued

17. A compound selected from the group consisting of:

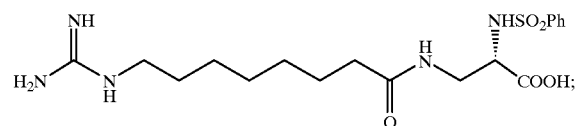

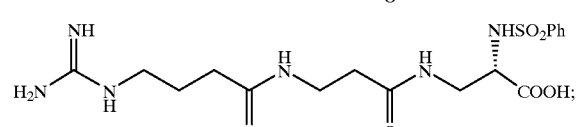

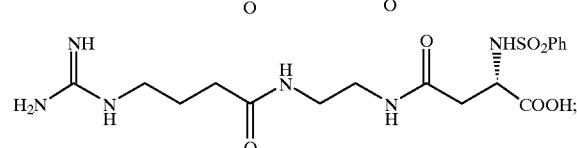

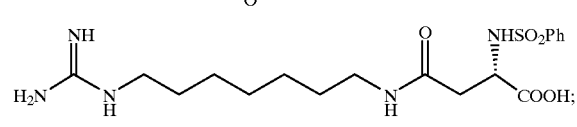

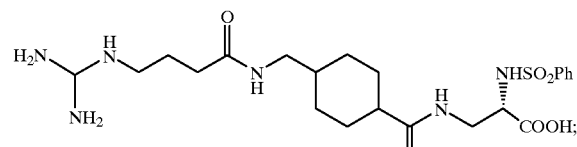

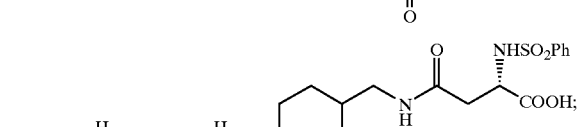

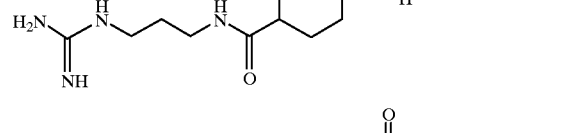

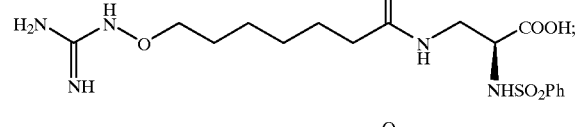

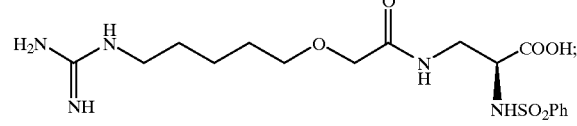

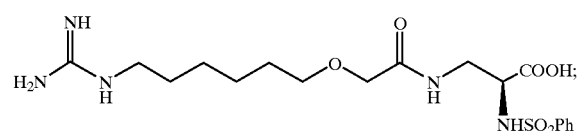

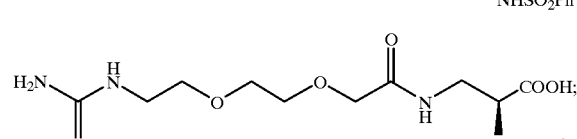

-continued

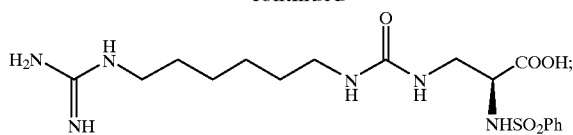

and

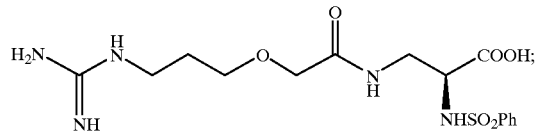

or a pharmaceutically acceptable stereoisomer, salt, solvate, hydrate, or prodrug derivative thereof.

18. A compound of claim 17, selected from the group consisting of:

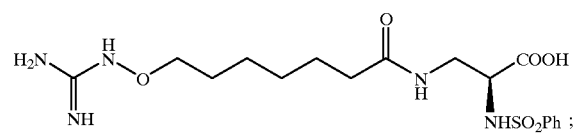

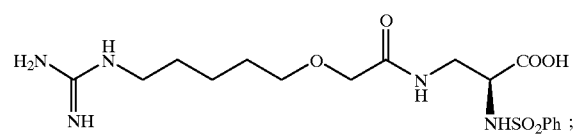

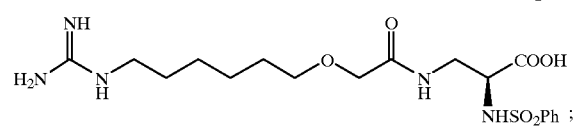

and

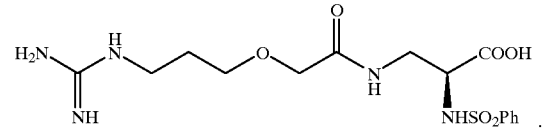

19. A compound of claim 17, selected from the group consisting of:

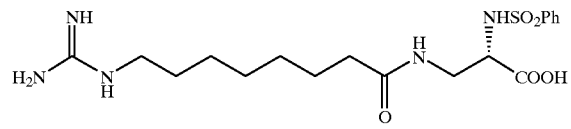

and

-continued

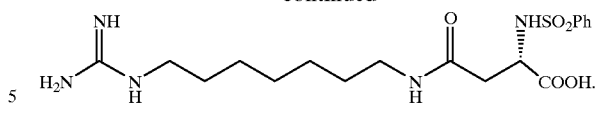

20. A compound of claim 17, selected from the group consisting of:

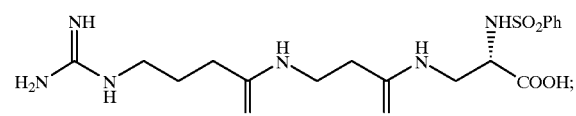

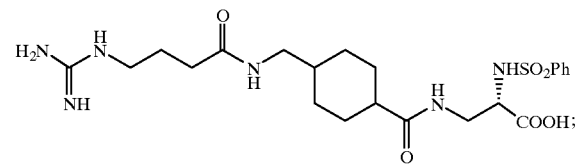

and

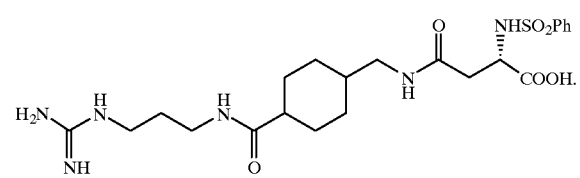

21. A pharmaceutical composition for preventing or treating a condition in a mammal characterized by undesired thrombosis comprising a therapeutically-acceptable carrier and a therapeutically-effective amount of a compound of claim 17.

22. A method for preventing or treating a condition in a mammal characterized by undesired thrombosis comprising administering to said mammal a therapeutically-effective amount of a compound of claim 17.

23. The method of claim 22, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, vascularization of solid tumors and retinopathy.

* * * * *